(12) United States Patent
Zhang et al.

(10) Patent No.: US 8,703,437 B2
(45) Date of Patent: Apr. 22, 2014

(54) FLUOROGENIC SENSORS FOR PHOSPHOLIPASE C ISOZYMES

(75) Inventors: Qisheng Zhang, Chapel Hill, NC (US); Wei Gang Huang, Chapel Hill, NC (US); John Sondek, Chapel Hill, NC (US); Stephanie Hicks, Hillsborough, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/703,274

(22) PCT Filed: Jun. 7, 2011

(86) PCT No.: PCT/US2011/039436
§ 371 (c)(1),
(2), (4) Date: Feb. 1, 2013

(87) PCT Pub. No.: WO2011/156366
PCT Pub. Date: Dec. 15, 2011

(65) Prior Publication Data
US 2013/0183701 A1 Jul. 18, 2013

Related U.S. Application Data

(60) Provisional application No. 61/353,461, filed on Jun. 10, 2010.

(51) Int. Cl.
C09B 57/00 (2006.01)
C09B 11/24 (2006.01)
C12Q 1/44 (2006.01)

(52) U.S. Cl.
USPC .......... 435/19; 435/4; 435/21; 544/1; 546/23; 546/22; 546/1

(58) Field of Classification Search
None
See application file for complete search history.

(56) References Cited

U.S. PATENT DOCUMENTS

| | | | |
|---|---|---|---|
| 5,726,025 A | 3/1998 | Kirschner et al. |
| 5,972,621 A | 10/1999 | Tartaglia et al. |
| 5,985,829 A | 11/1999 | Harris et al. |
| 6,015,692 A | 1/2000 | Gyuris et al. |

OTHER PUBLICATIONS

Birrell, G.B., et al., Biophys. J. 2003, 84, pp. 3264-3275.
Bleasdale et al., J. Pharmacol, Exp. Ther. 1990, 255, pp. 756-768.
Brynes et al., Anal. Biochem. 1981, 116, pp. 408-413.
Cocco et al., Adv. Enzyme Regul, 2005, 45, pp. 126-135 (Abstract Only).
Ellis, M.V., et al., J. Biol. Chem. 1998, 273, 11650-11659.
Floyd et al., Prog. Med. Chem. 1999, 36, pp. 91-168 (Abstract Only).
Gee et al., Cell Calcium 2007, 27, pp. 97-106 (Abstract Only).
Harden, et al., Annu. Rev. Pharmacol. Toxicol 2006, 46, pp. 355-379.
Hendrickson, E.K., et al., Bioorg. Med. Chem. Lett. 1991, 1, 619-623.
Hendrickson et al., Biochem. 1992, 31, pp. 12169-12172.
Hicks S.N., et al., Mol. Cell 2008, 31, pp. 383-394.
Kassis et al., Clin. Cancer Res. 1999, 5, pp. 2251-2260.
Kubiak, R.J., et al., J. Org, Chem. 2003, 68, pp. 960-968.
Lee, M.R., et al., Angew. Chem, Int. Ed. Engl. 2004, 43, pp. 1675-1678.
Lemmon, M.A., Nat. Rev. Mol. Cell Biol. 2008, 9, pp. 99-111.
Liu et al., ChemBioChem 8, pp. 1430-1439, 2007.
Matsushima et al., Alzheimer Dis. Assoc. Disord. 1995, 9, 213-217 (Abstract Only).
Pez, D., et al., Bioorg Med. Chem. 2003, 11, 4693-4711.
Rebecchi et al., J. Biol. Chem. 1993, 268, pp. 1735-1741.
Rhee, S.G., Annu. Rev. Biochem. 2001, 70, pp. 281-312.
Rose et al., Org. Lett. 2006, 8, pp. 2575-2578.
Rukavishnikov, A.V., et al., Bioorg. Med. Chem. Lett. 1999, 9, pp. 1133-1136.
Rusten et al., Nat. Methods 2006, 3, pp. 351-258.
Scholze et al., Anal. Biochem. 1999, 276, pp. 72-80 (Abstract Only).
Shepard et al., Oncogene 2007, 26, pp. 3020-3026.
Shi, T.J. et al., Proc. Nat.1 Acad. Sci. U.S.A. 2008, 105, 20004-20008.
Shimohama et al., Ann. N.Y. Acad. Sci. 1993, 695, pp. 46-49.
Tan et al., Am. Chem. Soc. 1998,120, pp. 8565-8566.
Wilsher et al., Drug. Metab. Dispos. 2007, 35, pp. 1017-1022.
Supplementary European Search Report and European Search Opinion, European Patent Application No. EP 11793014.9, mailed Oct. 16, 2013 (5 pages).
Ho et al. "A Self-Immolative Reporter for β-Galactosidase Sensing" *ChemBioChem* 8:560-566 (2007).
Huang et al. "A Fluorogenic, Small Molecule Reporter for Mammalian Phospholipase C Isozymes" *ACS Chem. Biol*. 6:223-228 (2011).
Richard et al. "Latent Fluorophores Based on a Self-Immolative Linker Strategy and Suitable for Protease Sensing" *Bioconjugate Chem*. 19:1707-1718 (2008).
Rukavishnikov et al. "Synthesis of a New Fluorogenic Substrate for the Assay of Phosphoinositide-Specific Phospholipase C." *Tetrahedron Letters* 39:6637-6640 (1998).
Schmidinger et al. "Novel Fluorescent Phosphonic Acid Esters for Discrimination of Lipases and Esterases" *ChemBioChem* 6:1776-1781 (2005).
Zaikova et al. "Synthesis of Fluorogenic Substrates for Continuous Assay of Phosphatidylinositol-Specific Phospholipase C" *Bioconjugate Chem*. 12:307-313 (2001).
PCT International Search Report for International Application No. PCT/US2011/039436, mailed Feb. 23, 2012 (6 pages).
International Preliminary Report on Patentability Corresponding to International Application No. PCT/US2011/039436; Date of Mailing: Dec. 20, 2012; 7 Pages.

*Primary Examiner* — Blaine Lankford
*Assistant Examiner* — David Berke-Schlessel
(74) *Attorney, Agent, or Firm* — Myers Bigel Sibley & Sajovec, PA

(57) ABSTRACT

The present invention provides fluorogenic substrates and methods of use in detecting and analyzing phospholipase C isozyme (PLC) activity.

42 Claims, 15 Drawing Sheets

FLUOROGENIC SENSORS FOR PHOSPHOLIPASE C ISOZYMES

RELATED APPLICATION DATA

This application is a 35 U.S.C. §371 national phase application of International Application Ser. No. PCT/US2011/039436, filed Jun. 7, 2011, which claims the benefit, under 35 U.S.C. §119(e), of U.S. Provisional Patent Application No. 61/353,461, filed Jun. 10, 2010, the disclosures of each of which are incorporated herein by reference in their entireties.

STATEMENT OF GOVERNMENT SUPPORT

Aspects of this invention were made with government support under National Institutes of Health Grant No. R01-GM057391. The United States Government has certain rights to this invention.

STATEMENT REGARDING ELECTRONIC FILING OF A SEQUENCE LISTING

A Sequence Listing in ASCII text format, submitted under 37 C.F.R. §1.821, entitled 5470-55_ST25.txt, 1,238 bytes in size, generated on Mar. 6, 2013 and filed via EFS-Web, is provided in lieu of a paper copy. This Sequence Listing is hereby incorporated by reference into the specification for its disclosures.

FIELD OF THE INVENTION

This application concerns compounds and methods for detecting and analyzing phospholipase C (PLC) activity.

BACKGROUND OF THE INVENTION

Phospholipase C isozymes (PLCs) catalyze the conversion of the membrane lipid phosphatidylinositol 4,5-bisphosphate ($PIP_2$) into two second messengers, inositol 1,4,5-trisphosphate ($IP_3$) and diacylglycerol (DAG) (Scheme 1).[1] $IP_3$ mobilizes intracellular stores of $Ca^{2+}$ while DAG activates protein kinase C.[2] Furthermore, depletion of $PIP_2$ alters the membrane association and/or activity of many proteins that harbor phosphoinositide binding domains.[3] Consequently, PLC isozymes are key signaling proteins that regulate the physiological responses of many extracellular stimuli such as hormones, neurotransmitters, and growth factors. Aberrant regulation of PLCs has been implicated in various diseases including cancer, Alzheimer's disease, and others.[4] Although extensive studies have been carried out to understand PLC regulation, two limitations remain: 1) it is difficult to monitor PLC activity in living cells; and 2) selective small molecule PLC inhibitors are lacking.[5]

Scheme 1. Cleavage of $PIP_2$ to $IP_3$ and DAG by PLC.

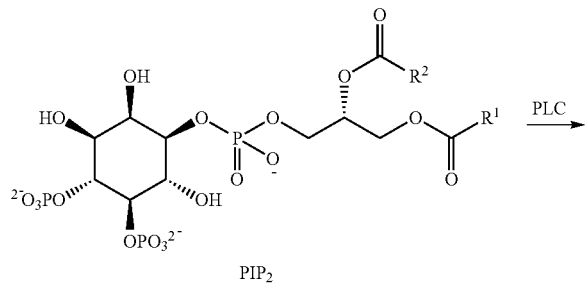

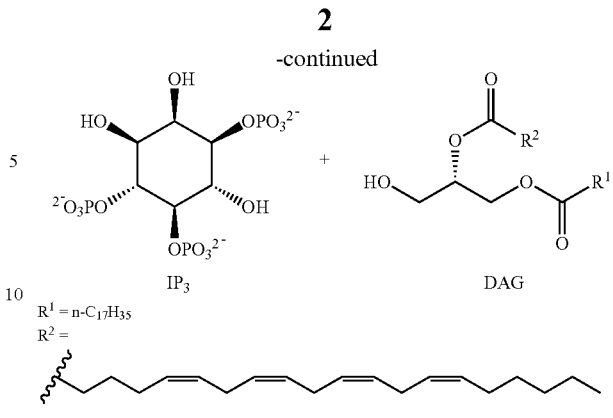

The present invention overcomes previous shortcomings in the art by providing compounds and methods for detecting phospholipase C (PLC) activity.

SUMMARY OF THE INVENTION

A first aspect of the present invention is a compound of Formula I:

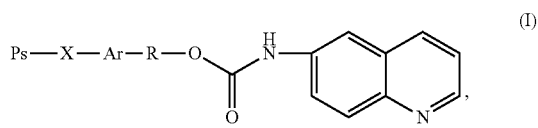

(I)

wherein:
Ps is a substrate for phospholipase C isozymes;
X is O or S;
Ar is an aromatic group which may be substituted with one or more functional groups selected from the group consisting of alkyl, alkenyl, alkynyl, hydroxy, hydroxyalkyl, alkoxy, aryloxy, alkylthio, amino, aminoalkyl, alkylamino, cycloalkyl, heteroaryl, heteroalkyl, aryl, arylalkyl, aliphatic oxide, $OC(=O)R_{10}$, $OC(=O)OR_{10}$, $OC(=O)N(R_{10})_2$, $O(CH_2)_mN(R_{10})_2$, $C(=O)N(R_{10})_2$, and $O(CH_2)_mCOOR_{10}$, where m is 1-20 and $R_{10}$ is H, alkyl, alkenyl, or alkynyl; and
R is alkyl, alkenyl, alkynyl, aryl, or arylalkyl.

A second aspect of the present invention is a compound of Formula II:

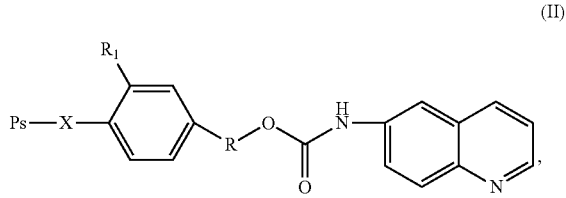

(II)

wherein:
Ps is a substrate for phospholipase C isozymes;
X is O or S;
R is alkyl, alkenyl, alkynyl, aryl, or arylalkyl; and
$R_1$ is selected from the group consisting of H, alkyl, alkenyl, alkynyl, hydroxy, hydroxyalkyl, alkoxy, aryloxy, alkylthio, amino, aminoalkyl, alkylamino, cycloalkyl, heteroaryl, heteroalkyl, aryl, arylalkyl, aliphatic oxide, $OC(=O)R_{10}$, $OC(=O)OR_{10}$, $OC(=O)N(R_{10})_2$, $O(CH_2)_mN(R_{10})_2$, $C(=O)N(R_{10})_2$, and $O(CH_2)_mCOOR_{10}$, where m is 1-20 and $R_{10}$ is H, alkyl, alkenyl, or alkynyl.

A further aspect of the present invention is a compound of Formula III:

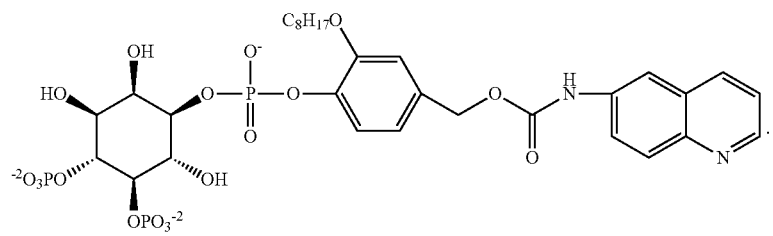

An additional aspect of the present invention is a compound of Formula IV:

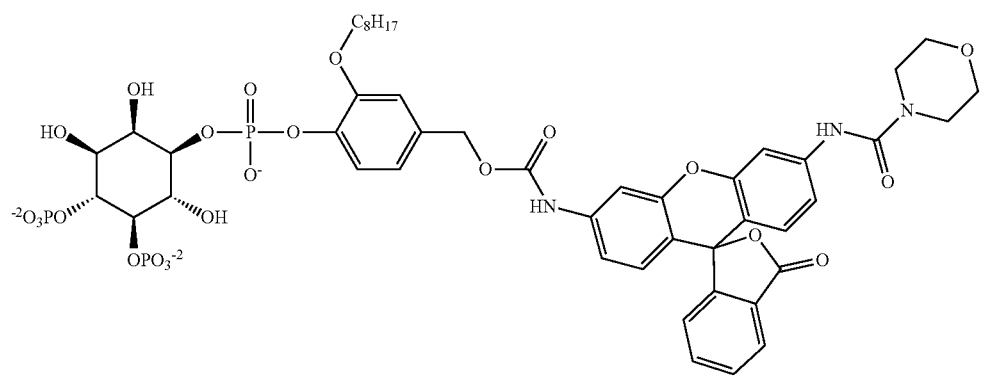

A further aspect of the present invention is a method of identifying a test substance that inhibits phospholipase C activity, comprising:

a) contacting a fluorogenic sensor of this invention (e.g., a compound of any of Formulas I-VII) with phospholipase C in the presence of a test substance, under conditions whereby fluorescence resulting from reaction of the fluorogenic sensor and phospholipase C can be detected, and detecting the amount of fluorescence;

b) contacting the fluorogenic sensor of (a) above with the phospholipase C of (a) above in the absence of the test substance, under conditions whereby fluorescence resulting from reaction of the fluorogenic sensor and phospholipase C can be detected, and detecting the amount of fluorescence;

c) comparing the amount of fluorescence detected in step (a) with the amount of fluorescence detected in step (b), whereby a decrease in the amount of fluorescence detected in step (a) identifies that the test substance inhibits phospholipase C activity.

A still further aspect of the present invention is a method of detecting phospholipase C activity in a cell, comprising:

a) contacting a fluorogenic sensor of this invention (e.g., a compound of any of Formulas I-VII) with a cell under conditions whereby fluorescence resulting from reaction of the fluorogenic sensor and phospholipase C can be detected; and b) detecting fluorescence in the cell, thereby detecting phospholipase C activity in the cell.

Another aspect of the present invention is a method of detecting aberrant phospholipase C activity in a cell, comprising:

a) contacting a fluorogenic sensor of this invention (e.g., a compound of any of Formulas I-VII) with a cell under conditions whereby fluorescence resulting from reaction of the fluorogenic sensor and phospholipase C can be detected;

b) detecting an amount or pattern of fluorescence in the cell; and c) comparing the amount or pattern of fluorescence detected in step (b) with the amount or pattern of fluorescence in a control cell that has been contacted with the fluorogenic sensor of step (a), whereby an alteration in the amount or pattern of fluorescence in the cell as compared with the control cell detects aberrant phospholipase C activity in the cell.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION OF THE INVENTION

Figure 1:
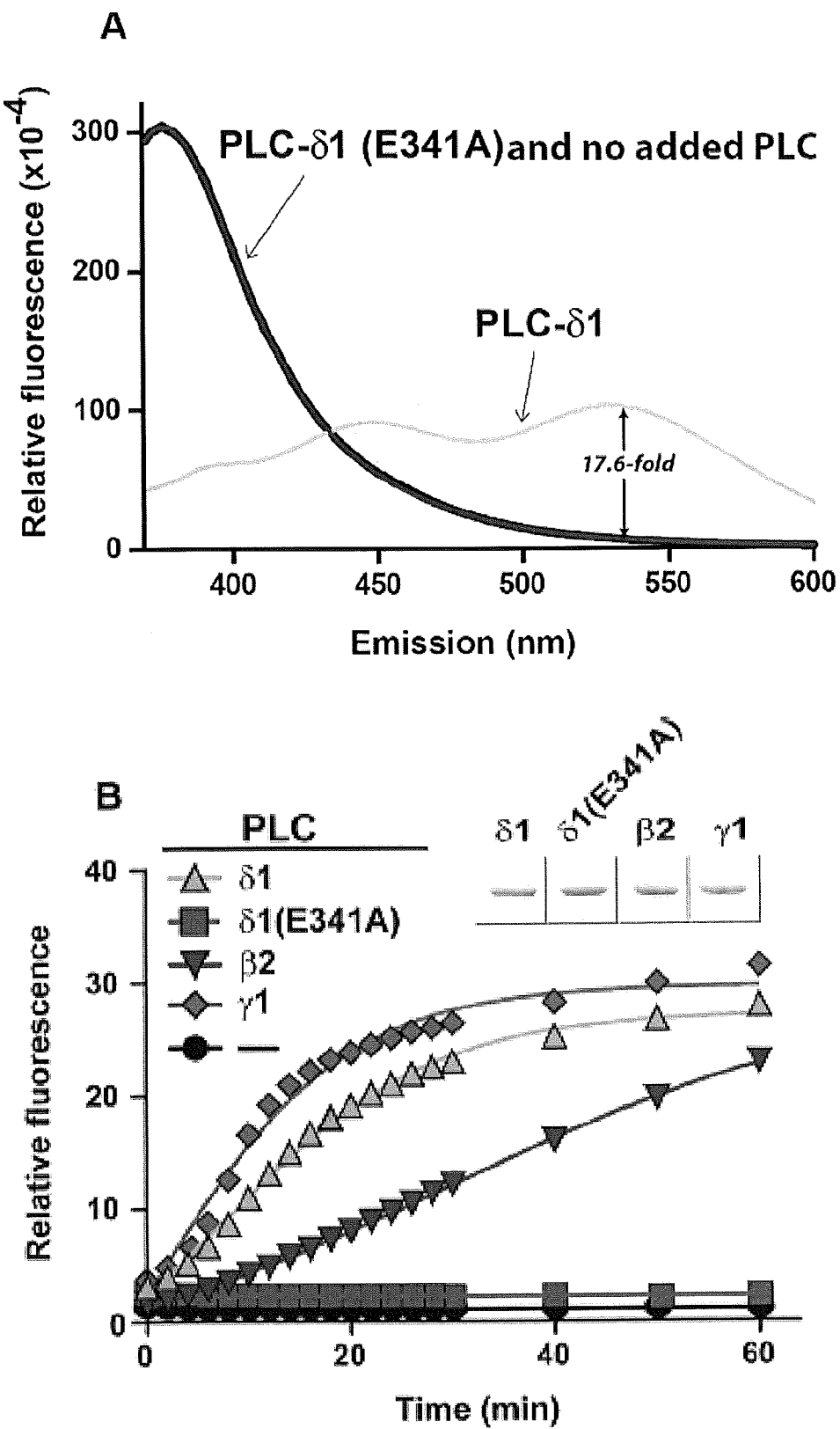
FIG. 1. (A) Emission spectra of the fluorogenic sensor WH-15 in the presence of either wild-type (light grey) or catalytically inactive (dark gray) PLC-δ1 or no added PLC (dark gray) for 60 min prior to recording of emission spectra ($\lambda_{ex}$=344 nm). The ~17.6-fold increase in emission at 535 nm between reactions with wild-type PLC-δ1 and no added PLC is also shown. (B) Real-time fluorescence of WH-15 cleavage catalyzed by different PLC isoforms and normalized to the initial fluorescence of the reaction without PLC. Equivalent amounts of purified PLCs (inset) were verified by SDS-PAGE followed by staining with Coomassie Brilliant Blue. Initial concentration of WH-15 (44 µM) and PLC isozymes (20 ng/15 µL) are the same in both panels.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "about," as used herein when referring to a measurable value such as an amount or concentration (e.g., the signal-to-background ratio) and the like, is meant to encompass variations of 20%, 10%, 5%, 1%, 0.5%, or even 0.1% of the specified amount.

I. Definitions

"Moiety" and "group" are used interchangeably herein to refer to a portion of a molecule, typically having a particular functional or structural feature, e.g., a linking group (a portion of a molecule connecting two other portions of the molecule).

"Substituted" as used herein to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group. The substituted group may contain one or more substituents that may be the same or different.

"Substituent" as used herein references a group that replaces another group in a chemical structure. Typical substituents include nonhydrogen atoms (e.g., halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include, but are not limited to, alkyl, lower alkyl, haloalkyl, alkenyl, alkynyl, cycloalkyl, cycloalkylalkyl, heterocyclo, heterocycloalkyl, aryl, arylalkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, boronyl, and modified lower alkyl.

"Alkyl" as used herein alone or as part of another group, refers to a straight or branched chain hydrocarbon containing from 1 to 20 carbon atoms. In some embodiments, the alkyl group may contain 1, 2, or 3 up to 4, 5, 6, 7, 8, 9, 10, 11, 12, 13, 14, 15, 16, 17, 18, 19, or 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from polyalkylene oxides (such as PEG), halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 20 carbon atoms (or in loweralkenyl 1 to 4 carbon atoms) which include 1 to 10 double bonds in the hydrocarbon chain. In some embodiments, the alkenyl group may contain 1, 2, or 3 up to 4, 5, 6, 7, 8, 9, 10, 11, 12, 13, 14, 15, 16, 17, 18, 19, or 20 carbon atoms. Representative examples of alkenyl include, but are not limited to, methylene (=CH$_2$), vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups such as those described in connection with alkyl and loweralkyl above.

"Alkynyl" as used herein alone or as part of another group, refers to a straight or branched chain hydrocarbon containing from 1 to 20 carbon atoms (or in loweralkynyl 1 to 4 carbon atoms) which include at least one triple bond in the hydrocarbon chain. In some embodiments, the alkynyl group may contain 2, or 3 up to 4, 5, 6, 7, 8, 9, 10, 11, 12, 13, 14, 15, 16, 17, 18, 19, or 20 carbon atoms. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Aliphatic group" as used herein alone or as part of another group refers to a straight-chain, branched-chain, or cyclic aliphatic hydrocarbon group and includes saturated and unsaturated aliphatic groups, such as an alkyl group, an alkenyl group, and an alkynyl group, as defined herein. The aliphatic group may be unsubstituted or substituted with one or more substituents, which may be the same or different. When substituted at both ends, or utilized as part of a chain or "backbone," such groups may also be known as alkylene, alkenylene, and alkynylene groups. In some embodiments, the aliphatic group may contain 1, 2, or 3 up to 4, 5, 6, 7, 8, 9, 10, 11, 12, 13, 14, 15, 16, 17, 18, 19, or 20 carbon atoms.

"Aliphatic oxide group" as used herein refers to an aliphatic group as defined herein substituted with one or more oxygen atoms. The aliphatic oxide group may be unsubstituted or substituted with one or more substituents, which may be the same or different. In some embodiments, the aliphatic oxide group may contain 2 or 3 up to 4, 5, 6, 7, 8, 9, 10, 11, 12, 13, 14, 15, 16, 17, 18, 19, or 20 carbon and oxygen atoms. In some embodiments the aliphatic oxide group may be utilized as part of a chain or "backbone," which may comprise, consist of, or consist essentially of an aliphatic group containing from 1 to 10 carbon atoms, then an oxygen atom, followed by another aliphatic group containing from 1 to 10 carbon atoms, wherein the oxygen atom and aliphatic group may be repeated 1, 2, 3, 4, 5, 6, 7, 8, 9, or 10 times and the aliphatic groups may be the same or different.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Aromatic group" as used herein alone or as part of another group, refers to aromatic hydrocarbons (i.e., "aryl") and heteroaromatic rings (i.e., "heteroaryl"). The aromatic group may be unsubstituted or substituted with one or more substituents, which may be the same or different. If substituted with one or more substitutents the substituents may be at any location on the aromatic group. For instance, in some embodiments the substitutents are in a 1,2 (ortho) and/or 1,4 (para) configuration. Exemplary aromatic hydrocarbons include, but are not limited to, phenyl, as well as bicyclic (e.g., naphthalene), tricyclic (e.g., phenanthrene, anthracene) or higher aromatic hydrocarbons. Exemplary heteroaromatic rings include, but are not limited to, 2,4-imidazole, -thiazole, and -oxazole and 2,5-pyrrole, -furan, and -thiophene. Also included are fused counterparts, i.e., polycyclic aromatic groups containing a 5-membered heteroaromatic ring.

"Aryl" as used herein alone or as part of another group, refers to a monocyclic carbocyclic ring system or a bicyclic carbocyclic fused ring system or higher having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Arylalkenyl" as used herein alone or as part of another group, refers to an aryl group, as defined herein, appended to the parent molecular moiety through an alkenyl group, as defined herein.

"Arylalkynyl" as used herein alone or as part of another group, refers to an aryl group, as defined herein, appended to the parent molecular moiety through an alkynyl group, as defined herein.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Heteroaryl" as used herein is as described in connection with heterocyclo and aryl above.

"Heteroalkyl" as used herein by itself or in combination with another term, means, unless otherwise stated, a stable straight or branched chain, or cyclic hydrocarbon radical (e.g., "heterocycloalkyl" or "heteroarylalkyl"), or combinations thereof, comprising an alkyl group, as defined herein, and at least one heteroatom selected from the group consisting of O, N, and S, and wherein the nitrogen, carbon and sulfur atoms may optionally be oxidized and the nitrogen heteroatom may optionally be quaternized. The heteroatom(s) O, N and S may be placed at any interior position of the alkyl group or at the position at which the alkyl group is attached to the remainder of the molecule. Up to two heteroatoms may be consecutive, such as, for example, —CH$_2$—NH—OCH$_3$. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

"Alkoxy" as used herein alone or as part of another group, refers to an alkyl or loweralkyl group, as defined herein (and thus includes substituted versions such as polyalkoxy), and is appended to the parent molecular moiety through an oxy group, —O—, Representative examples of alkoxy include, but are not limited to, methoxy, ethoxy, propoxy, 2-propoxy, butoxy, tert-butoxy, pentyloxy, hexyloxy and the like.

"Aryloxy" as used herein alone or as part of another group refers to an aryl group, as defined herein (and thus includes substituted versions), and is appended to the parent molecular moiety through an oxy group, —O—.

"Hydroxyalkyl" as used herein alone or as part of another group refers to a hydroxyl group, as defined herein, appended to the parent molecular moiety through an alkyl group as defined herein (and thus includes substituted versions). Representative examples of hydroxyalkyl include, but are not limited to, hydroxymethyl, hydroxyethyl, hydroxypropyl and the like.

"Halo" as used herein refers to any suitable halogen, including F, Cl, Br and I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" or "carboxy" as used herein alone or as part of another group, refers to a —C(O)OH group.

"Hydroxy" as used herein alone or as part of another group, refers to an —OH group.

"Nitro" as used herein refers to an —NO$_2$ group.

"Oxo" as used herein, refers to a =O moiety.

"Oxy," as used herein refers to a —O— moiety.

"Thio," as used herein refers to a —S— moiety.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein refers to the radical —$NH_2$.

"Alkylamino" as used herein alone or as part of another group refers to the radical —NHR, where R is an alkyl group.

"Aminoalkyl," as used herein refers to an alkyl group which is further substituted with one or more amino groups.

II. Fluorogenic Sensors

The present invention is directed to fluorogenic sensors that detect phospholipase C (PLC) activity upon cleavage by PLC. The fluorogenic sensors comprise, consist of, or consist essentially of a substrate for PLC covalently coupled to a linker group and a fluorophore. A substrate for phospholipase C isozymes as used herein refers to a chemical molecule or biological molecule, such as a phospholipid or glycolipid, that can be cleaved by phospholipase C. The substrate may be natural, synthetic, or an analog thereof. Substrates for phospholipase C include, but are not limited to, inositol phosphate, phosphatidylinositol, glycosylphosphatidylinositol, or analogs thereof. Specific exemplary substrates include, but are not limited to, inositol 1,4,5-triphosphate, D-myo-inositol 1,4-diphosphate, D-myo-inositol 1,2-cyclic phosphate, inositol phosphate analogues, and glycosylphosphatidylinositol analogues.

The linker group comprises an aromatic group, as defined herein. In some embodiments the linker group is designed to minimize the potential perturbation of the PLC active site by the fluorophore. In other embodiments the linker group is designed to undergo a 1,6-elimination reaction upon cleavage of the substrate by PLC. The 1,6-elimination reaction in some embodiments allows for the fluorophore to become active (i.e., result in detectable fluorescence), such as, but not limited to, by the cleavage of a quencher from the fluorogenic sensor. In other embodiments the 1,6-elimination reaction results in the cleavage of the fluorophore from the fluorogenic sensor. The linker group in some embodiments may comprise a substituent that provides or enhances the hydrophobic or hydrophilic character of the fluorogenic sensor. In some embodiments the linker group comprises a substituent, as defined herein, that retains the hydrophobic character of the fluorogenic sensor, while still allowing for the fluorogenic sensor to be water soluble. Exemplary substituents that retain the hydrophobic character of the fluorogenic sensor, while still allowing for the fluorogenic sensor to be water soluble include, but are not limited to, alkyl, alkenyl, alkynyl, aryl, or arylalkyl.

Fluorophores of the present invention are chemical compounds, which when excited by exposure to a particular wavelength of light, emit light (fluoresce), for example at a different wavelength of light. Also encompassed by the term "fluorophore" are luminescent molecules, which are chemical compounds that do not require exposure to a particular wavelength of light to fluoresce; luminescent compounds naturally fluoresce. In some embodiments the fluorophore is covalently coupled to the substrate or the linker group.

Numerous fluorophores are known in the art and may be utilized in the present invention. Exemplary fluorophores include, but are not limited to, fluoresceins, such as TET (Tetramethyl fluorescein), 2',7'-dimethoxy-4',5'-dichloro-6-carboxyfluorescein (JOE), 6-carboxyfluorescein (HEX) and 5-carboxyfluorescein (5-FAM); phycoerythrins; resorufin dyes; coumarin dyes; rhodamine dyes, such as 6-carboxy-X-rhodamine (ROX); cyanine dyes; BODIPY dyes; quinolines; pyrenes; N,N,N',N'-tetramethyl-6-carboxyrhodamine (TAMRA); acridine; stilbene; Texas Red; as well as derivatives thereof. In some embodiments the fluorophore is a rhodamine dye or a BODIPY dye and in other embodiments the fluorophore is 6-aminoquinoline.

Exemplary fluorogenic sensors of the present invention include a compound of Formula I:

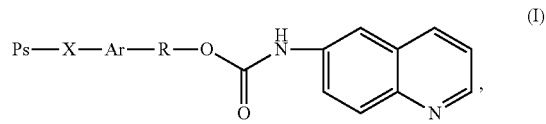

(I)

wherein:
Ps is a substrate for phospholipase C isozymes;
X is O or S;
Ar is an aromatic group which may be substituted with one or more functional groups selected from the group consisting of alkyl, alkenyl, alkynyl, hydroxy, alkoxy, alkylthio, amino, aminoalkyl, alkylamino, heteroaryl, heteroalkyl, aryl, arylalkyl, aliphatic oxide, OC(=O)$R_{10}$, OC(=O)O$R_{10}$, OC(=O)N($R_{10}$)$_2$, O(CH$_2$)$_m$N($R_{10}$)$_2$, C(=O)N($R_{10}$)$_2$, and O(CH$_2$)$_m$COO$R_{10}$, where m is 1-20 and $R_{10}$ is H, alkyl, alkenyl, or alkynyl; and
R is alkyl, alkenyl, alkynyl, aryl, or arylalkyl.

Additional exemplary fluorogenic sensors include a compound of Formula II:

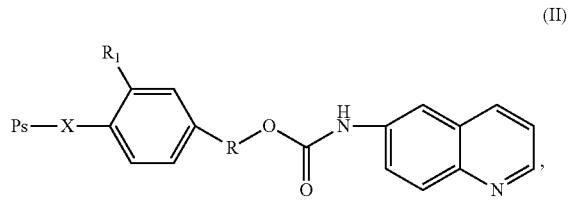

(II)

wherein:
Ps is a substrate for phospholipase C isozymes;
X is O or S;
R is alkyl, alkenyl, alkynyl, aryl, or arylalkyl; and
$R_1$ is selected from the group consisting of H, alkyl, alkenyl, alkynyl, hydroxy, hydroxyalkyl, alkoxy, aryloxy, alkylthio, amino, aminoalkyl, alkylamino, cycloalkyl, heteroaryl, heteroalkyl, aryl, arylalkyl, aliphatic oxide, OC(=O)$R_{10}$, OC(=O)O$R_{10}$, OC(=O)N($R_{10}$)$_2$, O(CH$_2$)$_m$N($R_{10}$)$_2$, C(=O)N($R_{10}$)$_2$, and O(CH$_2$)$_m$COO$R_{10}$, where m is 1-20 and $R_{10}$ is H, alkyl, alkenyl, or alkynyl.

Other exemplary fluorogenic sensors include, but are not limited to, a compound of Formula III:

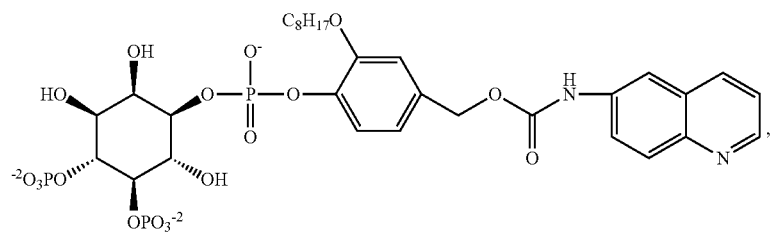

and a compound of Formula IV:

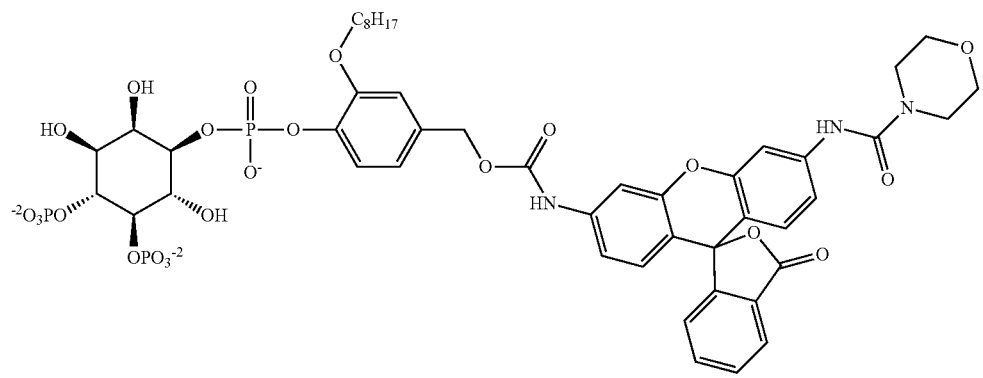

In one embodiment of the present invention, the fluorogenic sensors when in contact with PLC will be cleaved by PLC to generate in tandem reaction products of the cleavage. The reaction products of the PLC cleavage comprise, consist of, or consist essentially of the substrate for PLC, the fluorophore, and/or an aromatic group. Optional reaction products comprise, consist of, or consist essentially of a cellular localization signal and/or a quencher.

In some embodiments of the present invention, PLC cleaves the substrate (Ps) to initiate a 1,6-elimination reaction (Scheme 2). The 1,6-elimination reaction involves the movement of the bonds around the aromatic group upon cleavage of the Ps-X bond, as exemplified in Formula I and Formula II, by PLC. For the exemplary fluorogenic sensor of Formula III in Scheme 2 upon cleavage by PLC at the Ps-O bond, a 1,6-elimination reaction results that generates in tandem inositol triphosphate ($IP_3$, i.e., the substrate (Ps)), the aromatic group quinomethide 1, carbon dioxide, and the fluorescent compound 6-aminoquinoline 2.

Scheme 2. 1,6-elimination reaction of exemplary fluorogenic sensor of Formula III upon PLC cleavage.

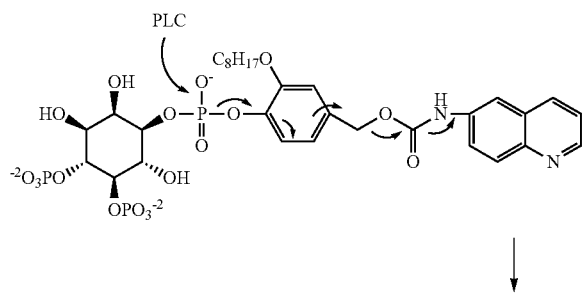

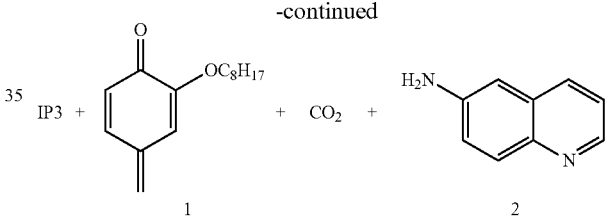

The fluorogenic sensor in some embodiments may further comprise a cellular localization signal, a photocage group, and/or a quencher.

"Cellular localization signal" as used herein refers to a signal that is used to direct the fluorogenic sensor to various distinguishable parts, components or organelles of a cell, including without limitation, the nucleus, cytoplasm, plasma membrane, endoplasmic reticulum, Golgi apparatus, filaments such as actin and tubulin filaments, endosomes, peroxisomes and mitochondria. Various cellular localization signals are known in the art and are commercially available. The cellular localization signal is an amino acid sequence that can be of any size and composition, for example 3 to 100 amino acids in length to, 4, 5, 6, 7, 8, 10, 12, 15, 20, 25, 30, 40, 50, 60, 70, 80, 90 or 100 amino acids in length. Cellular localization signals can be made by, for example, recombinant techniques or peptide synthesis. Exemplary cellular localization signals include, but are not limited to cytosol localization signals, nuclear localization signals, including but not limited to, SV40 virus T-antigen NLS and NLS sequences domain derived from viral Tat proteins, such as HIV Tat, and lysosomal localization signals, including but not limited to, lysosome associated membrane protein 1 (LAMP-1) tail sequence: RKRSHAGYQTI (SEQ ID NO:1); lysosomal acid phosphatase (LAP): RLKRMQAQPPGYRHVADGEDHAV (SEQ ID NO:2), and lysosomal integral membrane protein 2 (LIMP-2): RGQGSTDEGTADERAPLIRT (SEQ ID NO:3).

The cellular localization signal, when present, may be covalently coupled to any portion of the fluorogenic sensor, while still allowing for the PLC to act upon the substrate and for the fluorescent action of the fluorophore. There are different pools of PLCs in the cells that function differently. The cellular localization signal will dictate the location of the fluorogenic sensor and thus reports PLC activity at designated sites and/or organelles. As one of ordinary skill in the art would recognize, various moieties may be utilized to conjugate or couple the cellular localization signal to the fluorogenic sensor. In some embodiments the cellular localization signal is covalently coupled to the substrate for PLC (Ps) and/or to the fluorophore.

"Photocage group" as used herein refers to a group that prevents the fluorogenic sensor from functioning as a PLC substrate. The photocage group allows for the fluorogenic sensor to become activated at a certain point in time upon removal or modification of the photocage group. In some embodiments the photocage group allows for the fluorogenic sensor to be localized to a certain area of the cell. In other embodiments the photocage group allows for PLC activity to be monitored at set time points. For example, in cancer cells or other diseased cells or tissues where PLC activity is abnormally high, delivering PLC sensors into the cells may lead to the quick metabolism of the sensor. Incorporating photocage groups into the sensor will prevent it from functioning as a PLC substrate unless and until it is photo-decaged even though the sensor is delivered into the cells. The photocage group, when present, may be covalently coupled to any portion of the fluorogenic sensor, such that it prevents the fluorogenic sensor from acting as a substrate for PLC. As one of ordinary skill in the art would recognize, various moieties may be utilized to conjugate or couple the photocage group to the fluorogenic sensor. In some embodiments the photocage group is covalently coupled to the substrate for PLC (Ps).

"Quencher" as used herein refers to a chemical or biological compound that can absorb energy emitted by a fluorophore so as to reduce the amount of fluorescence emitted (i.e., quench the emission of the fluorescent label). Different fluorophores are quenched by different quenching agents. Quenchers are either non-fluorescent or fluorescent. Generally, non-fluorescent quenchers are capable of quenching the fluorescence of a wide variety of fluorophores, by absorbing energy from the fluorophore and releasing the energy as heat. Examples of non-fluorescent quenchers include, but are not limited to DABCYL, QSY-7, and QSY-33. Fluorescent quenchers are specific to fluorophores that emit at a specific wavelength range. In general, the spectral properties of a particular fluorophore/quenching agent pair are such that one or more absorption wavelengths of the quencher overlaps one or more of the emission wavelengths of the fluorophore. A preferred fluorophore/quencher pair can be selected by one of ordinary skill in the art by comparison of emission and excitation wavelengths. In some embodiments the quencher, when present, may be covalently coupled to any portion of the fluorogenic sensor, such that it quenches the fluorescence emission of the fluorophore. As one of ordinary skill in the art would recognize, various moieties may be utilized to conjugate or couple the quencher to the fluorogenic sensor. This design will allow the fluorescent group to stay where the sensor is localized, which is desirable for imaging PLC activity in real-time under both normal cellular environments and external stimulation. In some embodiments the quencher is separated from the fluorogenic sensor upon PLC cleavage.

Exemplary fluorogenic sensors comprising a cellular localization signal and a photocage group include, but are not limited to compounds of Formula V:

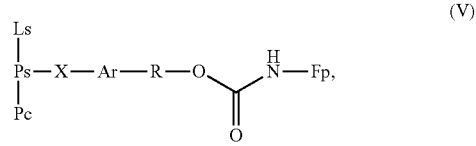

(V)

wherein:
Ps is a substrate for phospholipase C isozymes;
Pc is a photocage group;
Ls is a localization signal;
X is O or S;
Ar is an aromatic group which may be substituted with one or more functional groups selected from the group consisting of alkyl, alkenyl, alkynyl, hydroxy, hydroxyalkyl, alkoxy, aryloxy, alkylthio, amino, aminoalkyl, alkylamino, cycloalkyl, heteroaryl, heteroalkyl, aryl, arylalkyl, aliphatic oxide, $OC(=O)R_{10}$, $OC(=O)OR_{10}$, $OC(=O)N(R_{10})_2$, $O(CH_2)_mN(R_{10})_2$, $C(=O)N(R_{10})_2$, and $O(CH_2)_mCOOR_{10}$, where m is 1-20 and $R_{10}$ is H, alkyl, alkenyl, or alkynyl;
R is alkyl, alkenyl, alkynyl, aryl, or arylalkyl; and
Fp is a fluorophore.

Additional exemplary fluorogenic sensors include compounds of Formula VI:

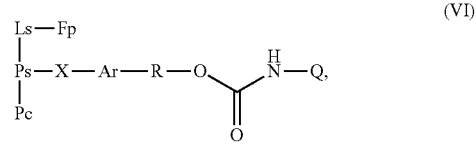

(VI)

wherein:
Ps is a substrate for phospholipase C isozymes;
Pc is a photocage group;
Ls is a localization signal;
Fp is a fluorophore;
X is O or S;
Ar is an aromatic group which may be substituted with one or more functional groups selected from the group consisting of alkyl, alkenyl, alkynyl, hydroxy, hydroxyalkyl, alkoxy, aryloxy, alkylthio, amino, aminoalkyl, alkylamino, cycloalkyl, heteroaryl, heteroalkyl, aryl, arylalkyl, aliphatic oxide, $OC(=O)R_{10}$, $OC(=O)OR_{10}$, $OC(=O)N(R_{10})_2$, $O(CH_2)_mN(R_{10})_2$, $C(=O)N(R_{10})_2$, and $O(CH_2)_mCOOR_{10}$, where m is 1-20 and $R_{10}$ is H, alkyl, alkenyl, or alkynyl;
R is alkyl, alkenyl, alkynyl, aryl, or arylalkyl; and
Q is a quencher.

Another exemplary fluorogenic sensor is a compound of Formula VII:

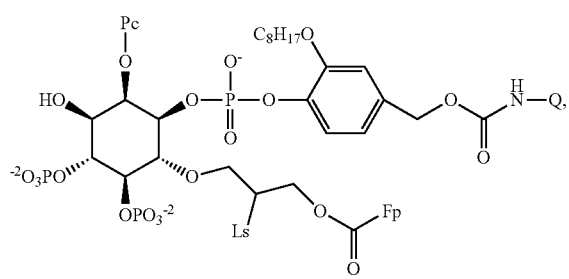

(VII)

wherein:
Pc is a photocage group;
Ls is a localization signal;
Fp is a fluorophore; and
Q is a quencher.

The fluorogenic sensors of the present invention can be used to identify inhibitors of PLC. Thus, one aspect of the invention provides a method for identifying a test substance that inhibits phospholipase C activity, comprising:

a) contacting a fluorogenic sensor of this invention (e.g., a compound of any of Formulas I-VII) with phospholipase C in the presence of a test substance, under conditions whereby fluorescence resulting from reaction of the fluorogenic sensor and phospholipase C can be detected, and detecting the amount of fluorescence;

b) contacting the fluorogenic sensor of (a) above with the phospholipase C of (a) above in the absence of the test substance, under conditions whereby fluorescence resulting from reaction of the fluorogenic sensor and phospholipase C can be detected, and detecting the amount of fluorescence;

c) comparing the amount of fluorescence detected in step (a) with the amount of fluorescence detected in step (b), whereby a decrease in the amount of fluorescence detected in step (a) identifies that the test substance inhibits phospholipase C activity.

The test substance can be any chemical or biological compound. The test substance may be natural or synthetic. The test substance can vary in size from small organic molecules to peptides or large proteins. In some embodiments the test compound is a small molecule. Protocols for the production, selection and testing of small molecules for their inhibitory effects are routine and well known in the art and can be readily adapted to the methods of this invention by one of ordinary skill in the art. The present invention further provides a method of screening small molecule libraries to identify a small molecule that inhibits PLC activity and/or function. Small molecule libraries can be obtained from various commercial entities, for example, SPECS and BioSPEC B.V. (Rijswijk, the Netherlands), Chembridge Corporation (San Diego, Calif.), Comgenex USA Inc., (Princeton, N.J.), Maybridge Chemical Ltd. (Cornwall, UK), and Asinex (Moscow, Russia). One representative example is known as DIVERSet™, available from ChemBridge Corporation, 16981 Via Tazon, Suite G, San Diego, Calif. 92127. DIVERSet™ contains between 10,000 and 50,000 drug-like, hand-synthesized small molecules. The compounds are pre-selected to form a "universal" library that covers the maximum pharmacophore diversity with the minimum number of compounds and is suitable for either high throughput or lower throughput screening For descriptions of additional libraries, see, for example, Tan et al. "Stereoselective Synthesis of Over Two Million Compounds Having Structural Features Both Reminiscent of Natural Products and Compatible with Miniaturized Cell-Based Assays" *J. Am. Chem Soc.* 120, 8565-8566, 1998; Floyd et al. *Prog Med Chem* 36:91-168, 1999. Numerous libraries are commercially available, e.g., from AnalytiCon USA Inc., P.O. Box 5926, Kingwood, Tex. 77325; 3-Dimensional Pharmaceuticals, Inc., 665 Stockton Drive, Suite 104, Exton, Pa. 19341-1151; Tripos, Inc., 1699 Hanley Rd., St. Louis, Mo., 63144-2913, etc. In certain embodiments of the invention the screening methods are performed in a high-throughput format using techniques that are well known in the art, e.g., in multiwell plates, using robotics for sample preparation and dispensing, etc. Representative examples of various screening methods may be found, for example, in U.S. Pat. Nos. 5,985,829, 5,726,025, 5,972,621, and 6,015,692. The skilled practitioner will readily be able to modify and adapt these methods as appropriate. In some embodiments the small molecule has a molecular weight of more than about 10 Daltons and less than about 5,000 Daltons, of more than about 40 Daltons and less than about 3,000 Daltons, or of more than about 100 Daltons and less than about 2,500 Daltons. Exemplary small molecules include, but are not limited to, peptides, peptoids, proteins, nucleotides, oligonucleotides, oligosaccharides, pharmaceuticals, sugars, fatty acids, steroids, derivatives, structural analogs, or combinations thereof.

The fluorogenic sensors of the present invention may also be used to detect PLC activity in a cell. The method of detecting phospholipase C activity in a cell, comprising:

a) contacting a fluorogenic sensor of this invention (e.g., a compound of any of Formulas I-VII) with a cell under conditions whereby fluorescence resulting from reaction of the fluorogenic sensor and phospholipase C can be detected; and b) detecting fluorescence in the cell, thereby detecting phospholipase C activity in the cell.

The cell can be any cell in which the absence, presence, or amount of PLC activity is desired to be determined. Such cells can be from any source, such as but not limited to mammalian and bacterial sources. Generally the cells are from mammalian subjects, such as but not limited to, human subjects, dogs, cats, horses, cows, sheep, monkeys, and chimpanzees.

An additional application for the fluorogenic sensors of the present invention may be for detecting aberrant PLC activity in a cell. The method of detecting aberrant phospholipase C activity in a cell, comprising:

a) contacting a fluorogenic sensor of this invention (e.g., a compound of any of Formulas I-VII) with a cell under conditions whereby fluorescence resulting from reaction of the fluorogenic sensor and phospholipase C can be detected;

b) detecting an amount or pattern of fluorescence in the cell; and c) comparing the amount or pattern of fluorescence detected in step (b) with the amount or pattern of fluorescence in a control (e.g., normal) cell that has been contacted with the fluorogenic sensor of step (a), whereby an alteration in the amount or pattern of fluorescence in the cell as compared with the control cell detects aberrant phospholipase C activity in the cell.

The cell can be any cell as described above. In some embodiments the cell is a diseased cell or a cell from a subject known to have or suspected of having a disease. In other embodiments the cell is from a subject at risk of having a disease. In one aspect of the present invention, the disease is a disease in which aberrant regulation of PLCs has been implicated. The disease may be caused by aberrant regulation of PLCs, correlated with aberrant regulation of PLCs, associated with aberrant regulation of PLCs, or linked to aberrant regulation of PLCs. In other embodiments of the present invention aberrant regulation of PLCs is suspected to be involved with the disease or to contribute to the disease. Exemplary diseases include, but are not limited to cancer such as but not limited to leukemia, prostate cancer, colorectal cancer, and breast cancer; neurodegenerative disease such as but not limited to Alzheimer's disease, Pick's disease, progressive supranuclear palsy, and diffuse Lewy body disease; ischemia; neuropathic pain; Down Syndrome; cardiovascular diseases such as but not limited to Tangier disease; and bone diseases. Exemplary cells include, but are not limited to, tumor cells, brain cells, nerve cells, glial cells, endothelial cells, myocardial cells, osteoblasts, and stem cells (including, but not limited to, embryonic and adult stem cells).

When detecting aberrant PLC activity in a cell (e.g., a diseased cell or a cell from a subject suspected or at risk of having or known to have a disease), the alteration in the amount or pattern of fluorescence may be an increase in the amount of fluorescence in the cell as compared with the control cell. Alternatively, the alteration in the amount or pattern of fluorescence may be a decrease in the amount of fluorescence in the cell as compared to the control cell.

In further embodiments, the fluorogenic sensors of the present invention may be used as a diagnostic tool for various PLC-related diseases, such as but not limited to cancer. As discussed above, in some embodiments the disease is a disease in which aberrant regulation of PLCs has been implicated. The disease may be caused by aberrant regulation of PLCs, correlated with aberrant regulation of PLCs, associated with aberrant regulation of PLCs, or linked to aberrant regulation of PLCs. In other embodiments of the present invention aberrant regulation of PLCs is suspected to be involved with the disease or to contribute to the disease. Additionally, the fluorogenic sensors may be used to detect a PLC-related disease, to monitor the treatment of a PLC-related disease, to monitor the progression of a PLC-related disease, and/or to diagnose a PLC-related disease. The fluorogenic sensors may also be used to determine if a subject has an increased or decreased risk of having a PLC-related disease.

As one of ordinary skill in the art would recognize, if the fluorogenic sensor comprises a photocage group, then any method utilizing the fluorogenic sensor may further comprise releasing or modifying the photocage group to allow for the fluorogenic sensor to function as a PLC substrate. The photocage group may be released or modified by any method known in the art, such as but not limited to cleavage. Exemplary types of cleavage include, but are not limited to enzymatic cleavage by enzymes such as peptidases, proteases, nucleases, lipases, or sequence specific restriction enzymes; chemical cleavage by a chemical agent that may cause the photocage group to dissociate, hydrolyze, or cleave when contacted with the chemical agent; cleavage by environmental cues, such as, for example, changes in temperature, pH, salt concentration, when there is such a change in environment following endocytosis, or by being exposed to energy, such as light, microwave, ultrasound, and radiofrequency.

The methods of the present invention may further comprise activating phospholipase C in the cell with a phospholipase C activator. Any chemical or biological agent or compound that activates PLC may be used. Many different chemical and biological agents or compounds activate PLC activity, but many induce different physiological responses. Accordingly, a specific PLC activator may be used depending on the method or the physiological response of interest. Exemplary PLC activators include, but are not limited to, neurotransmitters, growth hormones, drugs that activate membrane receptors, and growth factors. In some embodiments the cells are stimulated with a neurotransmitter, a growth hormone, a growth factor, a membrane receptor agonist, or any combination thereof.

The fluorogenic sensors of the present invention may be directly contacted with PLC or vice versa. The fluorogenic sensors can be delivered to cells either in vivo or in vitro by any method known in the art. Exemplary methods for delivering the fluorogenic sensors to cells include, but are not limited to, microinjection, carrier protein histones, and protection of the phosphoric acids as their esters.

In some embodiments of the present invention the fluorescence reaction of the fluorogenic sensors upon PLC cleavage has a signal-to-background (S/B) ratio of at least about 5, 6, 7, 8, 9, 10, 11, 12, 13, 14, 15 or more and a Z' factor of at least about 0.4, 0.5, 0.6, 0.7, 0.8, 0.9, or 1.

In some embodiments, the fluorogenic sensor is non-fluorescent until cleaved by PLC to yield a fluorescent product. The fluorophores of the fluorogenic sensors may be quenched prior to PLC cleavage. Quenching of the fluorophore may be by another compound (i.e., a quencher) that is either present in the reaction mixture, such as but not limited to water, and later removed or modified to allow for the fluorophore to fluoresce. The quencher may alternatively be another compound that is covalently coupled to the fluorogenic sensor. This quencher may be released or modified by any method known in the art, such as but not limited to cleavage, as described above.

In other embodiments, prior to PLC cleavage, the fluorophore of the fluorogenic sensor has an emission maximum that is different from the emission maximum of the fluorophore after PLC cleavage. Thus, the unconjugated fluorophore experiences a shift in wavelength compared to the conjugated fluorophore. This shift may be a red shift or blue shift. The shift in wavelength may be at least about 30, 40, 50, 60, 70, 80, 90, 100, 110, 120, 130, 140, 150, 160, 170, 180, 190, 200 or more nanometers.

The present invention is explained in greater detail in the following non-limiting examples.

EXAMPLES

Example 1

The synthesis of a fluorogenic sensor, WH-15, (Scheme 3) began with compound 3, which was prepared in 2 steps from commercially available 4-(benzyloxy)-3-hydroxybenzaldehyde.[21] Phosphorylation of 3 with 1-benzyloxy-N,N,N',N'-tetraisopropylphosphinediamine generated 4 quantitatively. Benzylaldehyde 4 also served as the phosphorylation reagent for enantiomerically and diastereomerically pure inositol phosphate derivative 5,[8] which was converted to 6 after reaction with 4 and oxidation with tert-butylperoxide. Reduction of the aldehyde group in 6 to the corresponding benzylalcohol with sodium borohydride (NaBH$_4$) led to 7 in 95% yield. Coupling of 7 with N-(quinolin-6-yl)-1H-imidazole-1-carboxamide 8, which was synthesized from 6-aminoquinoline and 1,1'-carbonyldiimidazole, followed by removal of the protective groups with trimethylsilyl bromide (TMSBr) and MeOH then produced the free phosphatidylinositide WH-15. The reporter is stable for 2 months with storage at −20° C. as judged by analyses with liquid chromatography/mass spectrometry (LC-MS) and NMR.

Scheme 3. Synthesis of the fluorogenic sensor, WH-15.

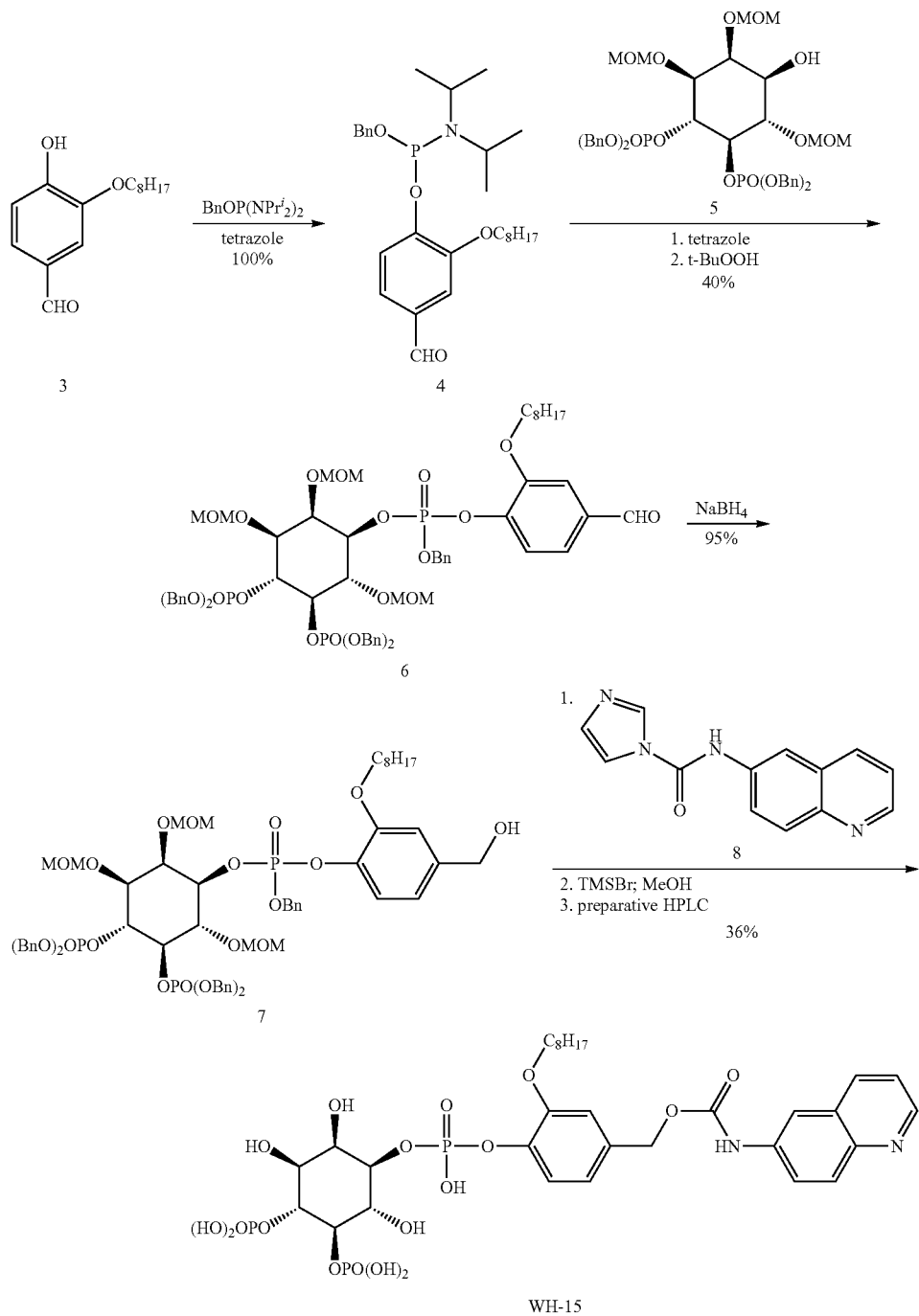

Figure 2:
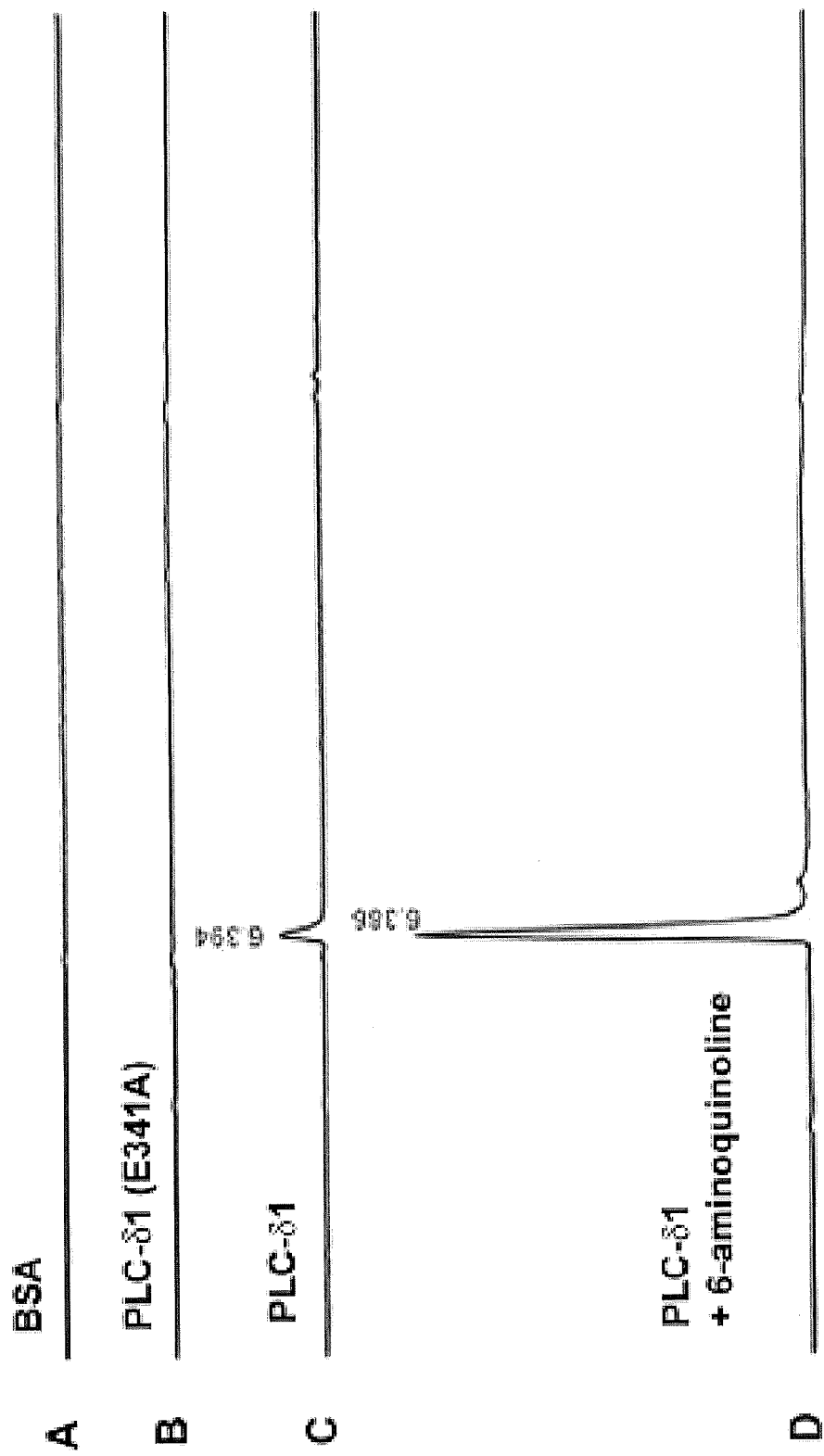
FIG. 2. The HPLC chromatograms for (A) BSA; (B) PLC-δ1(E341A); (C) PLC-δ1; and (D) co-injection of PLC-δ1 sample (20 µL) with 6-aminoquinoline (10 µL of 1.0 mM in H₂O) are shown. LC-MS (ESI-Pos) (E) analysis of the PLC-δ1 sample after incubation with WH-15 demonstrates the formation of a compound with the same molecular ion as 6-amino quinoline.
Figure 2:
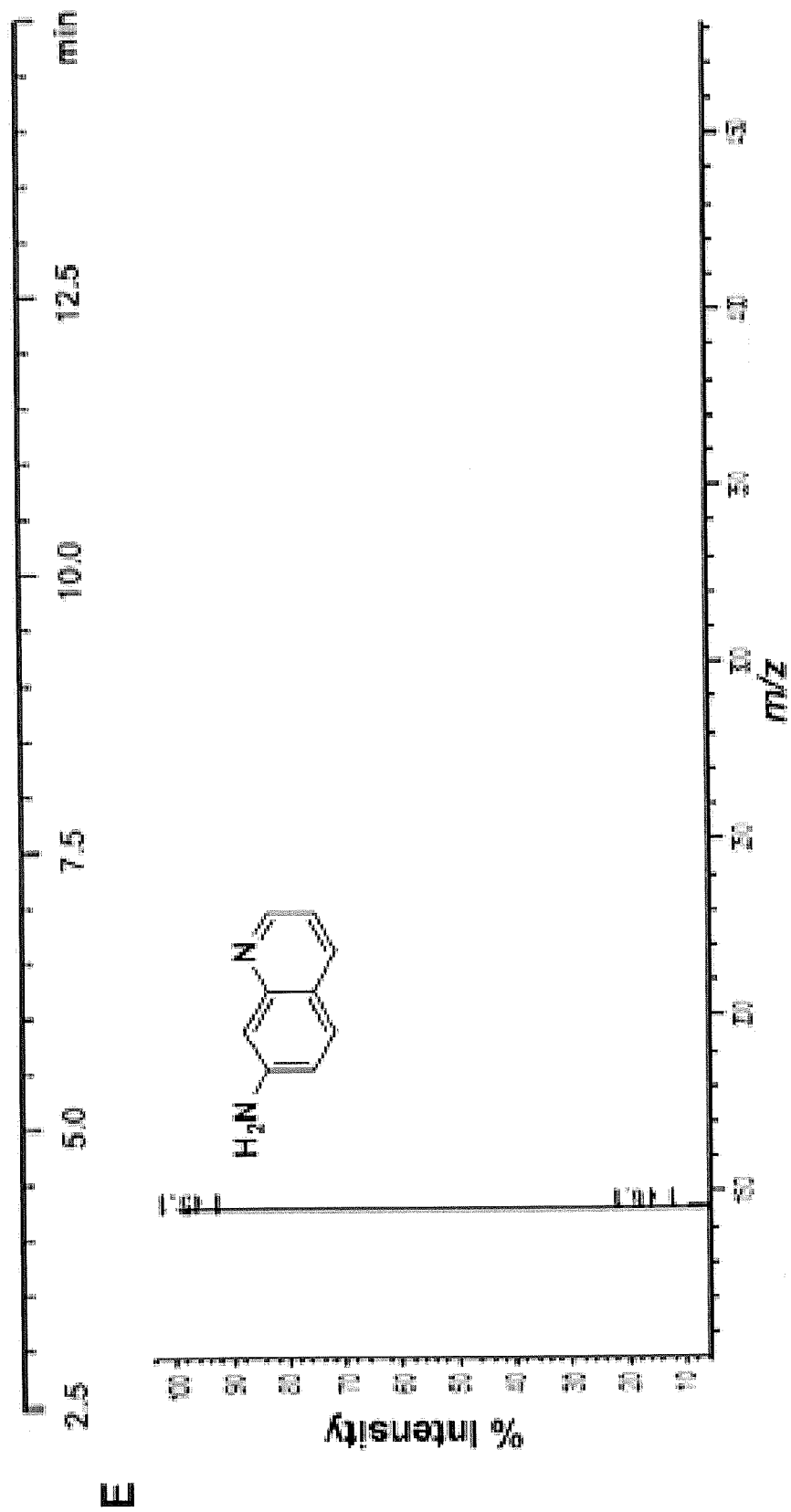

To demonstrate the application of this reporter, WH-15 was incubated with wild type, purified PLC-δ1 at 37° C. for 30 min and the emission spectrum of the reaction mixture was recorded. Purified PLC-61 harboring a single substitution (E341A) within its active site has immeasurable lipase activity and was used in a parallel reaction.[9] In addition, the reaction without PLC was also monitored. As shown in FIG. 1A, addition of wild type PLC-δ1 to the reaction mixture results in new emission peaks at 450 nm and 530 nm, consistent with the formation of 6-aminoquinoline measured by LC-MS, FIG. 2. In contrast, the reaction mixture with either PLC-δ1 (E341A) or no added PLC showed minimum emission at 530 nm and maximum emission at 380 nm (the emission spectra of PLC-δ1(E341A) and no added PLC, as shown in FIG. 1A, overlap), indicating that WH-15 was not cleaved by either PLC-δ1(E341A) or other components in the assay buffer. These results were further confirmed by LC-MS since 6-aminoquinoline 2 was not detected in the reaction mixture, FIG. 2. As demonstrated in FIG. 2, HPLC and LC-MS analyses confirm PLC-δ1 cleaves WH-15 to generate free 6-aminoquinoline. WH-15 (58 µM, final concentration) was used in the PLC assay buffer as described in the Experimental with the presence of BSA, PLC-δ1(E341A), or PLC-δ1. The reaction was stopped by adding MeOH and the mixture was analyzed by HPLC. The column was eluted in a gradient that starts with 10% MeOH in $H_2O$ and ends with 100% MeOH in 10 min.

To demonstrate that WH-15 can be used to monitor PLC activity, the real-time fluorescence of the reaction mixture was recorded for purified PLC-δ1 (FIG. 1B). WH-15 generated approximately a 30-fold increase in fluorescence with PLC-δ1 relative to an identically treated sample containing either catalytically inactive PLC-δ1 (E341A) or BSA. These results suggest that WH-15 specifically reports the enzymatic activity of PLC and the fluorescence-based assay is more sensitive and convenient than the traditional method.

Figure 3:
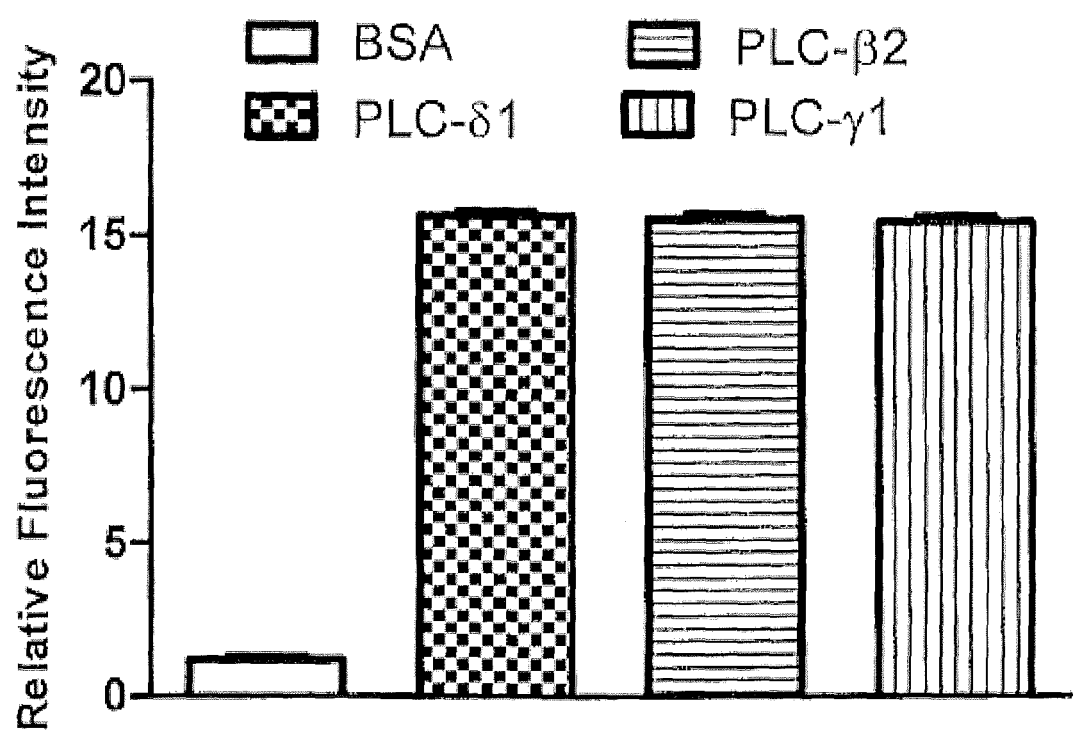
FIG. 3. Relative fluorescence intensity of PLC assays demonstrating that WH-15 is a reporter for mammalian PLC isozymes. The fluorescence of the reaction mixture was recorded 12 h after the reaction was initiated. The relative fluorescence intensity is defined as the ratio of fluorescence reading to the initial reading in the reaction mixture with BSA at t=0. Error bars are s.d.

The human genome encodes at least thirteen distinct PLCs.[1] To test whether WH-15 functions as a substrate for other PLC isoforms, the reporter was incubated with either purified PLC-β2 or PLC-γ1 in reactions analogous to that described for PLC-δ1. As shown in FIG. 1B, the fluorescence intensity of the reaction mixture with each of the three isoforms increases as reaction proceeds, suggesting that WH-15 is a substrate for all three isoforms of PLC tested. Although the kinetics profiles for the 3 isoforms are different, all reactions reach the same plateau in relative fluorescence intensity after incubation at 37° C. for 12 h, FIG. 3. These results suggest that WH-15 is a general substrate for different PLC isozymes.

Figure 4:
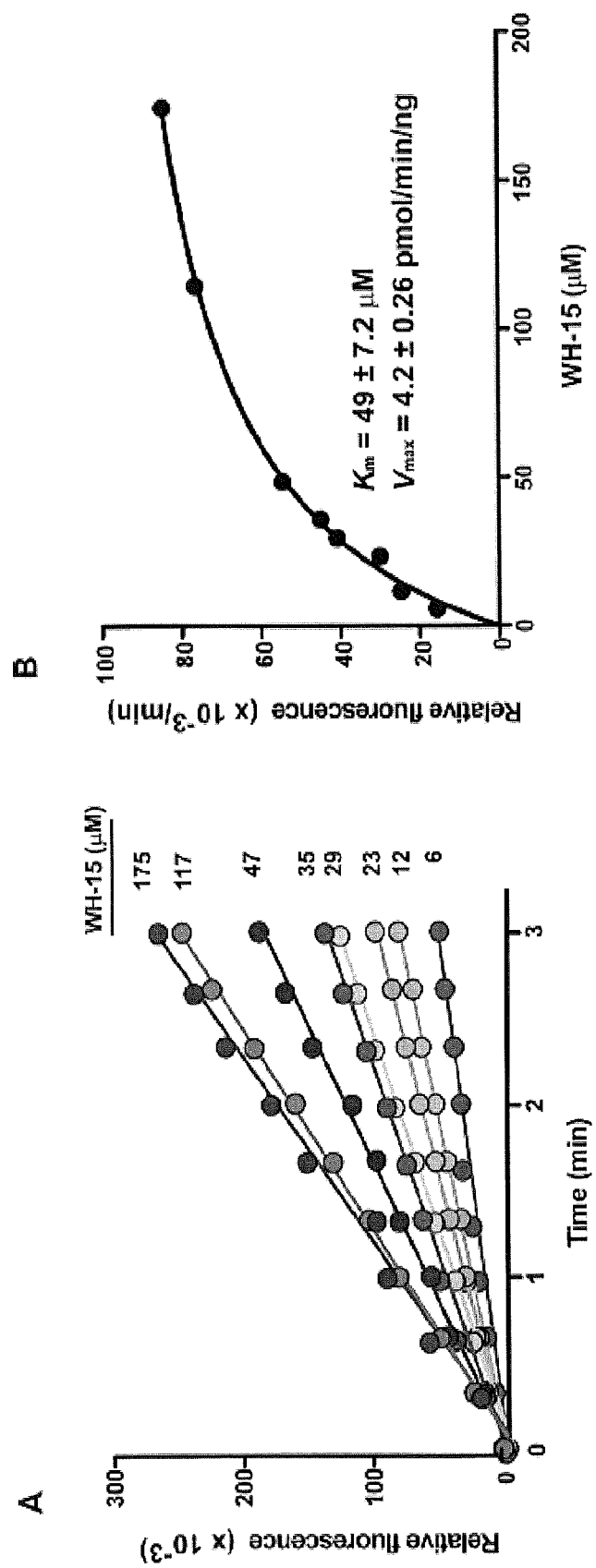
FIG. 4. Kinetic studies of WH-15 (A and B) and endogenous $PIP_2$ (C and D) with PLC-γ1.
Figure 4:
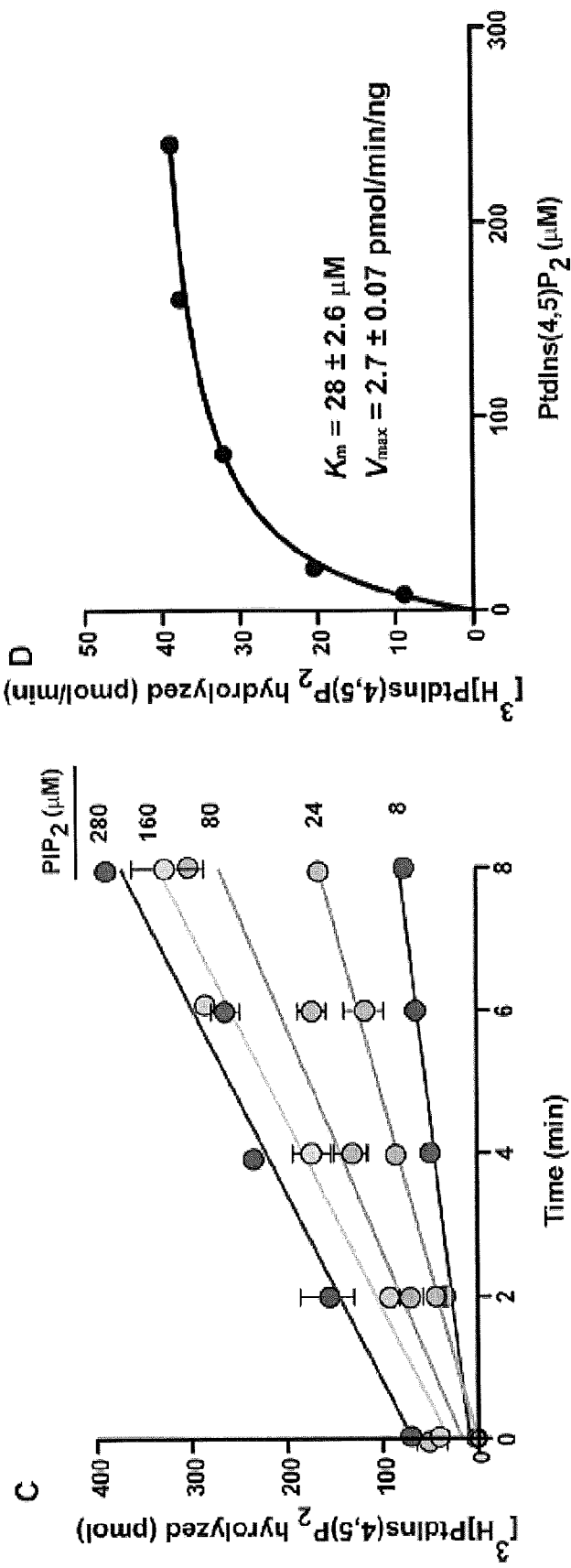
Figure 5:
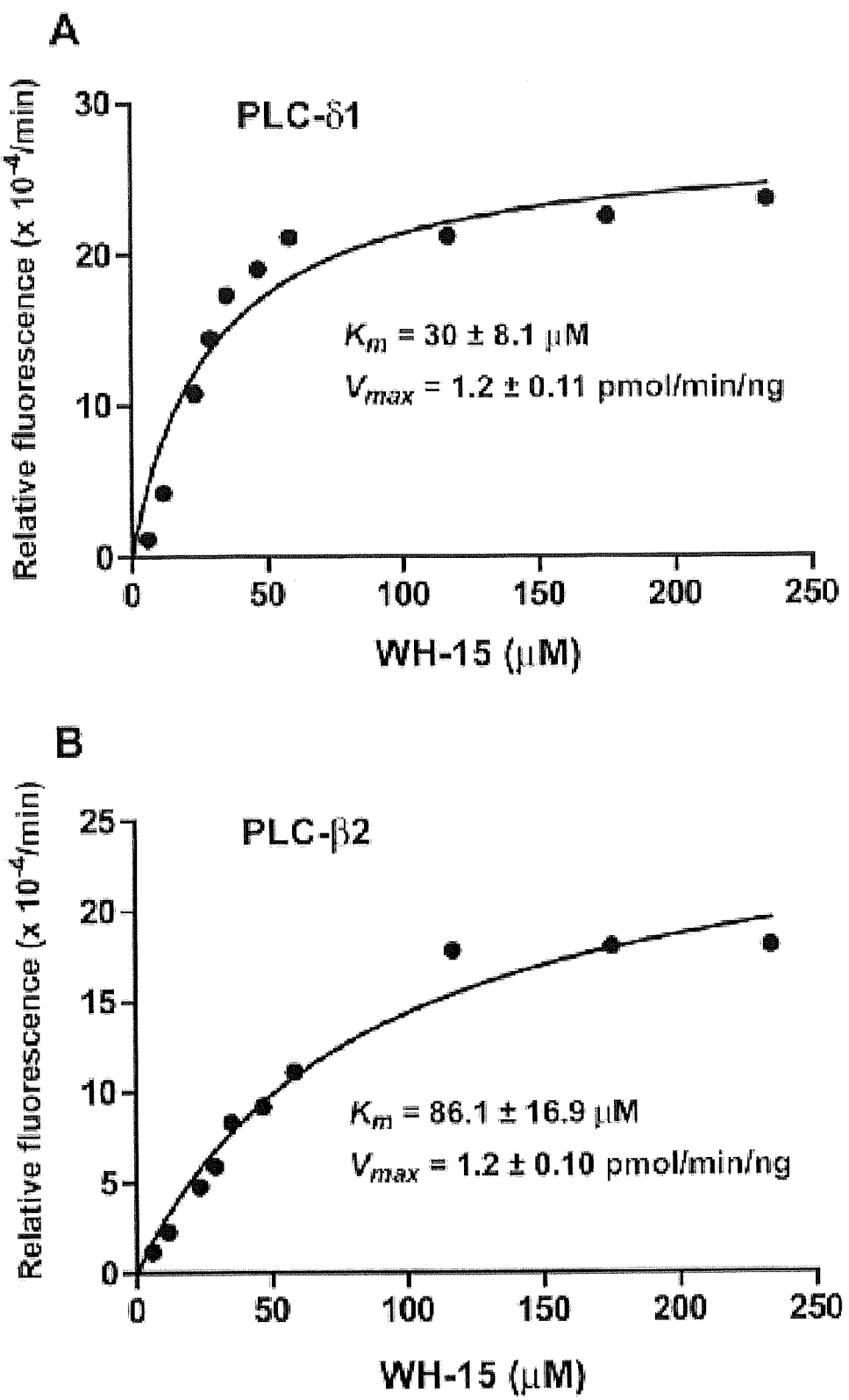
FIG. 5. Kinetic studies of WH-15 with PLC-M (A) and PLC-β2 (B).

To further characterize WH-15, the kinetic properties of WH-15 with PLC-γ1 were measured (FIG. 4). The $K_m$ of PLC-γ1 for WH-15 was 49±7.2 μM with a $V_{max}$ at 4.2±0.26 pmol/min/ng. For comparison, the endogenous substrate, $PIP_2$, was also applied in the enzymatic reaction under similar conditions. The $K_m$ was measured as 28±2.6 μM with a $V_{max}$ of 2.7±0.07 pmol/min/ng. Thus, despite the obvious structural differences between WH-15 and endogenous $PIP_2$, both molecules serve as essentially equivalent substrates for PLC-γ1 under the assay conditions. Furthermore, PLC-δ1 ($K_m$=30±8.1 μM; $V_{max}$=1.2±0.11 pmol/min/ng) and -β2 ($K_m$=86.1±16.9 μM; $V_{max}$=1.2±0.10 pmol/min/ng) hydrolyze WH-15 with similar kinetics, suggesting that all PLC isozymes will cleave WH-15 and $PIP_2$ with similar efficiencies (FIG. 5).

Figure 6:
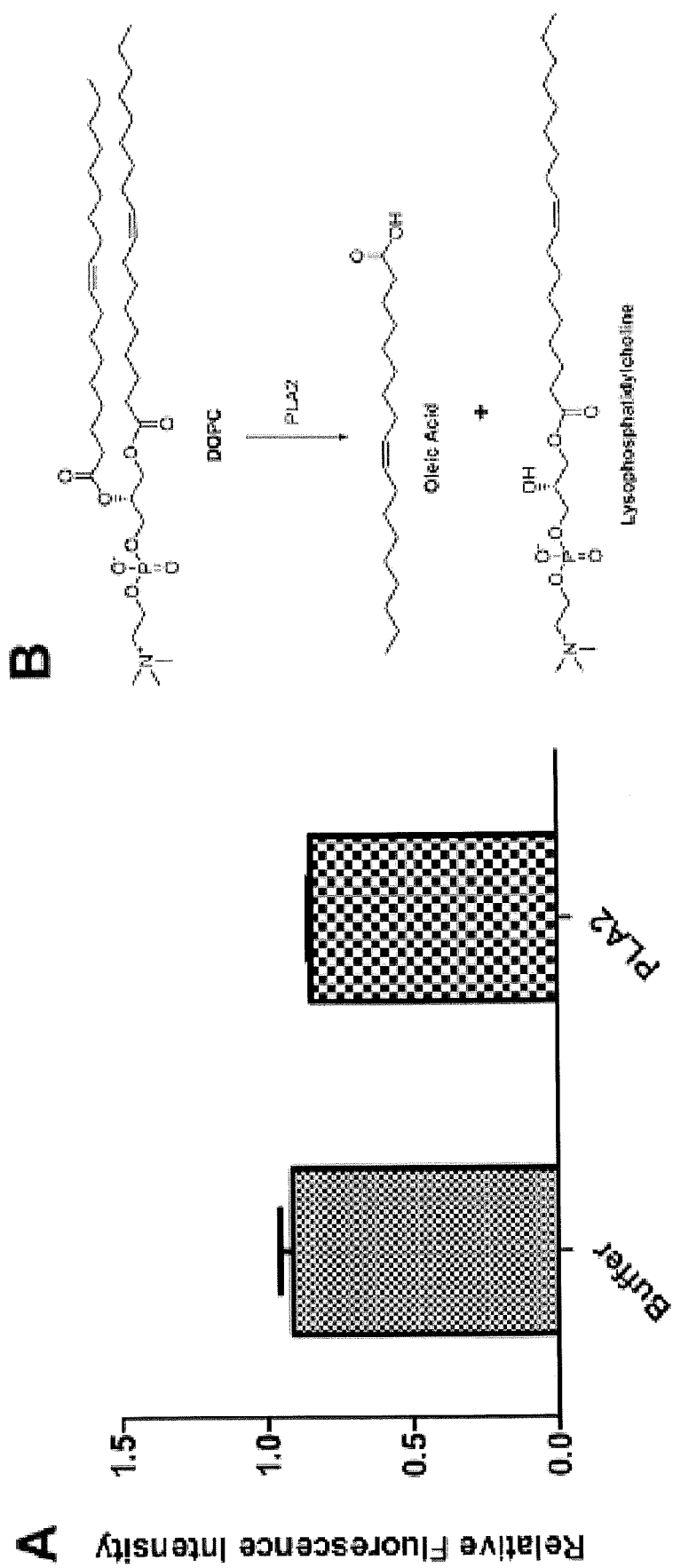
FIG. 6. (A) WH-15 was incubated with PLA2 under conditions that are described in Example 1 and fluorescence was recorded. The relative fluorescence intensity is defined as the ratio of fluorescence reading to the initial reading in reaction mixture without PLA2 at t=0 min, (B) The same batch of PLA2 catalyzed the hydrolysis of dioleoylphosphatidylcholine (DOPC) to olelic acid and lysophosphatidylcholine under the same reaction conditions. Lysophosphatidylcholine was detected by $^{31}$P-NMR and mass spectrometry (MS). The specific activity of PLA2 was measured as 5.9 nmol/min/unit. (C) WH-15 was incubated with PLD under conditions that are described in Example 1 and fluorescence was recorded. The relative fluorescence intensity is defined as the ratio of fluorescence reading to the initial reading in the reaction mixture without PLD at t=0 min. (D) The same batch of PLD catalyzed the hydrolysis of DOPC to dioleoylphosphatidic acid (DOPA) and choline under the same reaction conditions. DOPA was detected by $^{31}$P-NMR and MS. The specific activity of PLD was measured as 14.4 nmol/min/unit.
Figure 6:
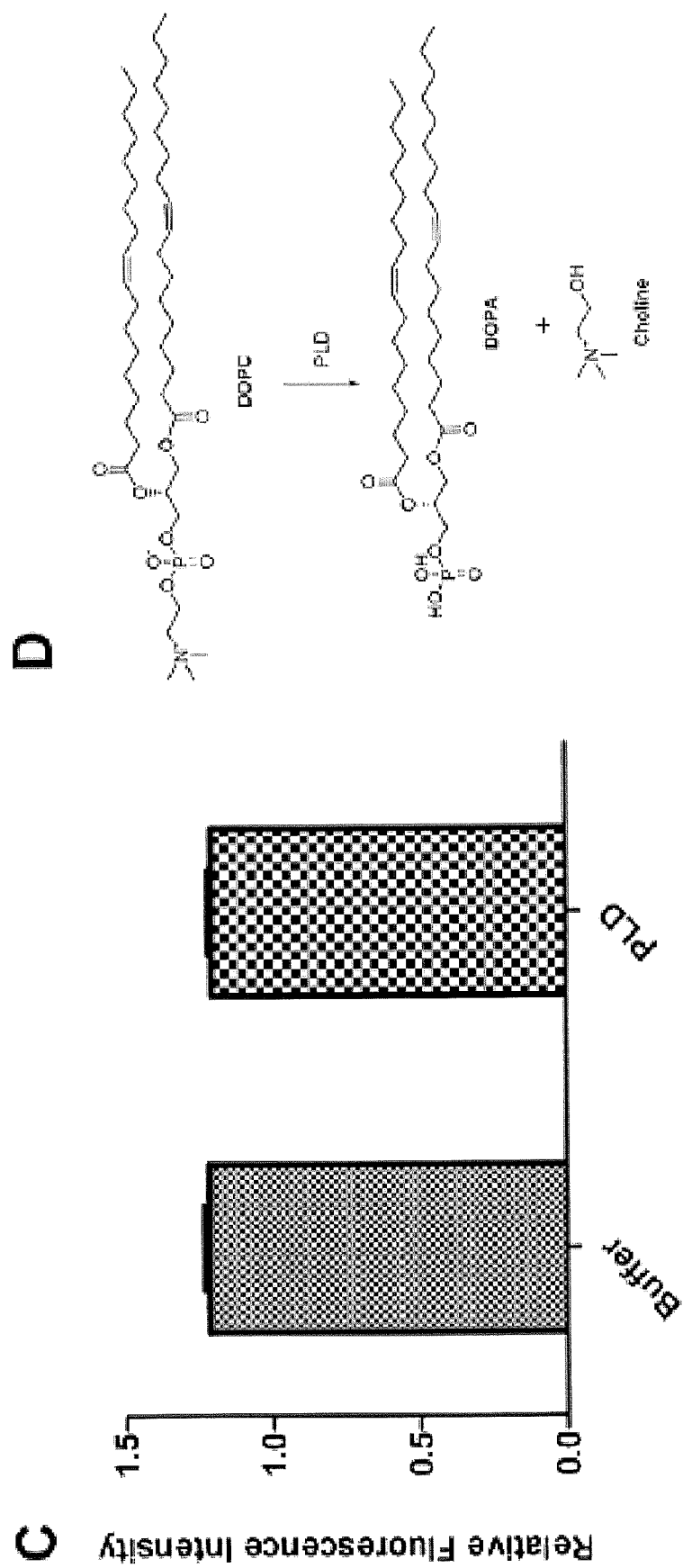

The reactive quinomethide intermediate formed upon the hydrolysis of WH-15 is unlikely to covalently modify PLC-γ1 to alter its phospholipase activity. Otherwise, nonlinear rates of WH-15 consumption would be expected, and this outcome is not observed. Instead, LC-MS analysis of the reaction mixture detected the formation of the products from reaction of quinomethide with dithiothreitol (DTT) and water, suggesting that quinomethide was most likely quenched by nucleophiles in the assay buffer. Substrate specificity of WH-15 for other related lipases was also tested. Two other phospholipases, phospholipase A2 (PLA2) and phospholipase D (PLD), did not generate fluorescence enhancement from WH-15 (FIG. 6), indicating that WH-15 is a PLC-selective fluorogenic reporter.

Figure 7:
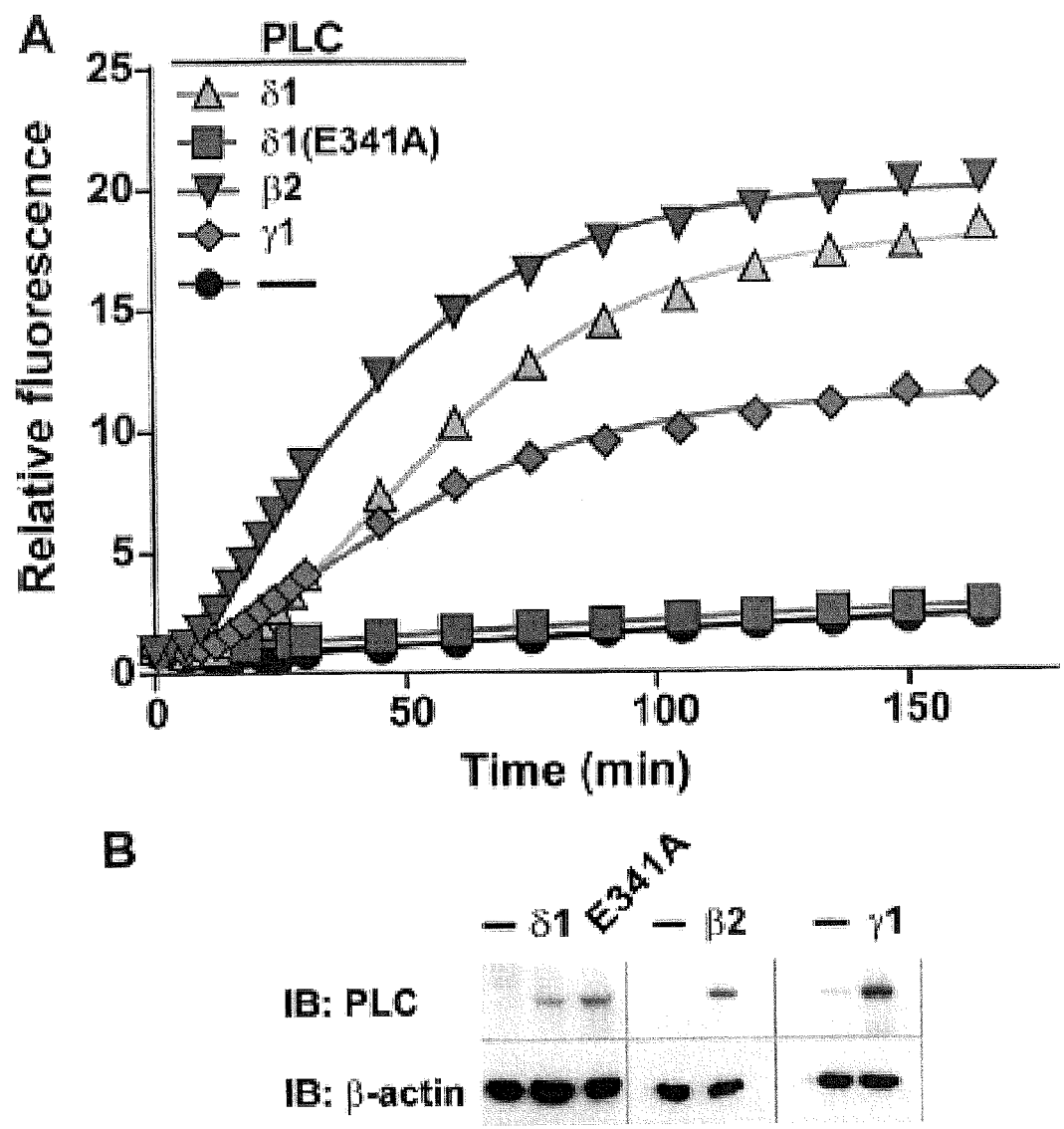
FIG. 7. (A) Real-time fluorescence of WH-15 (50 μM) cleavage catalyzed by PLC isozymes in cell lysates and normalized to the initial fluorescence of the reaction with lysates derived from cells transfected with empty vector. (B) HEK-293T cells were lysed and Western blotting was performed for the indicated PLC isozymes.

The function of WH-15 as a PLC reporter was next evaluated in cell lysates. Human Embryonic Kidney HEK-293T cells were transfected with plasmids encoding either PLC-δ1, PLC-δ1 (E341A), PLC-β2, PLC-γ1, or no PLC (empty vector control). After 24 h, the cells were lysed and equivalent amounts of cell lysates normalized for total protein were incubated with WH-15 and the real-time fluorescence was recorded and shown in FIG. 7A. As expected, cells transfected with empty vector generated minimal fluorescence enhancement as the basal level of endogenous PLC activity is low.[10] In addition, the cell lysate from the transfection of catalytically inactive PLC-δ1 (E341A) did not generate a fluorescence increase beyond the basal level, suggesting that the recorded fluorescence signal was dependent on the PLC enzymatic activity. These results confirm (i) the expected low basal activities of PLCs prior to upstream stimulation and (ii) that the cellular milieu does not contain substantial amounts of nonspecific phosphodiesterases capable of hydrolyzing WH-15. In contrast, cells transfected with PLC-δ1, PLC-β2, and PLC-γ1 show a 10-20 fold increase in fluorescence (FIG. 7A). Qualitative analysis of PLC overexpression in each lysate was assessed through Western blotting with monoclonal antibodies against PLC-δ1, PLC-β2, and PLC-γ1. As shown in FIG. 7B, cell lysates derived from the overexpression of PLC isoforms indeed possess a higher concentration of the enzymes compared to the lysate that was derived from cells transfected with empty vector. Taken together, these results demonstrate that WH-15 is a sensitive reporter for PLC activity in complex cell lysates. The fact that the fluorescence window is as large as 20-fold highlights the potential application of WH-15 in characterizing PLC activity in different cell lines.

In conclusion, a fluorogenic reporter WH-15 has been developed for mammalian PLC. This novel reporter functions in both enzymatic assays and cell lysates with high sensitivity, and represents a robust assay that is not based on radioactivity for mammalian PLCs. Given the key roles that PLCs play in cell signaling and diseases, this new PLC reporter will likely find broad applications in profiling different cell types and disease states. Furthermore, the large signal-to-background ratio of the assay with WH-15 will enable its use for high throughput screen of small molecule PLC inhibitors. WH-15 can also provide a starting point for developing fluorescent reporters to monitor PLC activities in real-time in cells.

Experimental

General

Chemicals were purchased from Aldrich and Acros Chemical Corporation and used without further purification. Solvents were purchased from suppliers as anhydrous grade. NMR spectra were recorded at room temperature on Gemini-300 MHz, Inova-400 MHz or Inova-500 MHz spectrometer. Chemical shifts are reported in ppm with TMS as the internal standard for $^1H$ NMR and 85% $H_3PO_4$ as the external standard for $^{31}P$ NMR spectra. High-resolution mass spectra were obtained on a Bruker Daltonics (Billerica, Mass.) BioToF (ESI-TOF; Electrospray Time of Flight Mass Spectrometer) mass spectrometer or a LTQ Orbitrap (Thermo Fisher Scientific, Bremen, Germany). HPLC analyses were performed on a Thermo Betasil C18 reverse phased column (150×4.6 mm, 5 μm) interfaced to a SHIMADZU LC-6AD system. Preparative HPLC was performed on a Thermo Betasil C18 reverse phase column (150×10 mm, 5 μm). Phospholipase $A_2$ from honey bee venom and Phospholipase D from *Streptomyces chromofuscus* were purchased from Sigma.

4-Hydroxy-3-(octyloxy)benzaldehyde (3)

To the solution of 4-(benzyloxy)-3-hydroxybenzaldehyde (190 mg, 0.83 mmol) in anhydrous DMF (2.0 mL) was added 60% NaH (40 mg, 1.00 mmol) at 0° C. followed by the addition of 1-iodooctane (300 mg, 1.25 mmol). The reaction mixture was stirred at room temperature (r.t.) overnight and $NH_4Cl$ solution was then added. The mixture was extracted with ethyl acetate 3 times and the combined organic layers were dried and concentrated under vacuum. The resulting residue was purified through flash column chromatography (Hexane:Ethyl Acetate=10:1) to yield 4-(benzyloxy)-3-(octyloxy)benzaldehyde (235 mg, 83%) as light yellow oil, which was subsequently subjected to hydrogenolysis in ethyl acetate in the presence of 10% Pd/C. After filtration and concentration, the crude residue was purified by column chromatography (Hexane:Ethyl Acetate=5:1) to give 3 (125 mg, 72%) as light yellow oil. $^1$H NMR (CDCl$_3$, 300 MHz) δ 9.80 (s, 1H), 7.36-7.42 (m, 2H), 7.03 (d, J=8.6 Hz, 1H), 6.44 (s, 1H), 4.09 (t, J=6.9 Hz, 2H), 1.82 (hexatet, J=6.7 Hz, 2H), 1.20-1.50 (m, 10H), 0.87 (t, J=6.8 Hz, 3H); $^{13}$C NMR (CDCl$_3$, 75 MHz) δ 191.09, 151.96, 146.70, 129.90, 127.42, 114.44, 109.68, 69.30, 31.86, 29.37, 29.28, 29.09, 26.03, 22.73, 14.17; ESI-HRMS for [M+H]$^+$ C$_{15}$H$_{23}$O$_3$: calcd 251.1647, found 5251.1638.

Benzyl 4-formyl-2-(octyloxy)phenyl diisopropylphosphoramidite (4)

A solution of phenol 1 (66.0 mg, 0.26 mmol) in anhydrous CH$_2$Cl$_2$ was added to the mixture of 1H-tetrazole (9.0 mg, 0.13 mmol) and 1-(benzyloxy)-N,N,N',N'-tetraisopropylphosphinediamine (1.0 M, in CH$_2$Cl$_2$) (0.53 mL, 0.53 mmol) at room temperature under argon. After stirring at room temperature (r.t.) for 3 h, the reaction mixture was concentrated and purified by column chromatography (Hexane:Acetone: TEA=100:5:3) to give phosphoramidite 4 (127 mg, 100%) as colorless oil. $^1$H NMR (CDCl$_3$, 300 MHz) δ 9.85 (s, 1H), 7.40 (d, J=2.1 Hz, 1H), 7.24-7.37 (m, 6H), 7.20 (dd, J=8.1 Hz, 1.8 Hz, 1H), 4.88 (dd, J=12.4, 8.5 Hz, 1H), 4.82 (dd, J=12.4, 8.5 Hz, 1H), 4.01 (t, J=6.5 Hz, 2H), 3.74-3.88 (m, 2H), 1.72-1.85 (m, 2H), 1.41-1.52 (m, 2H), 1.20-1.38 (m, 20H), 0.88 (t, J=7.3 Hz, 3H); $^{13}$C NMR (CDCl$_3$, 75 MHz) δ 191.33, 151.57 (d, J=2.3 Hz), 150.26 (d, J=4.4 Hz), 139.48 (d, J=7.4 Hz), 131.58, 128.39, 127.54, 127.09, 125.64, 120.10 (d, J=12.5 Hz), 111.17, 68.86, 66.09 (d, J=17.1 Hz), 43.85 (d, J=13.1 Hz), 31.92, 29.50, 29.37, 26.22, 24.71, 24.62, 24.50, 22.76, 14.20; $^{31}$P NMR (CDCl$_3$, 162 MHz) δ 149.01 (s, 1P); ESI-HRMS for [M+Na]$^+$ C$_{28}$H$_{42}$NO$_4$PNa: calcd 510.2749, found 510.2770.

Compound 6

A solution of phosphoramidite 4 (127 mg, 0.26 mmol) in anhydrous CH$_2$Cl$_2$ (2.0 mL) was added to compound 5 (65 mg, 78 μmol) and 1H-tetrazole (29 mg, 0.39 mmol) in anhydrous CH$_2$Cl$_2$ (1.0 mL) at r.t. in one portion under argon. The mixture was stirred at r.t. for 12 h, and a solution of t-BuOOH (5.0~6.0 M, 0.24 mL) in decane was added at −40° C. The resulting reaction mixture was warmed to room temperature gradually, concentrated and purified by column chromatography (Hexane:Acetone=2:1) to provide the product 6 (39 mg, 40%) as colorless oil. $^1$H NMR (CDCl$_3$, 400 MHz) δ 9.90 (s, 1H), 7.53 (dd, J=8.5, 8.2 Hz, 1H), 7.20-7.45 (m, 27H), 5.26 (conformation 1) and 5.24 (conformation 2) (2H), 4.85-5.15 (m, 9H), 4.57-4.80 (m, 4H), 4.51 (d, J=6.6 Hz, 1H), 4.32-4.45 (m, 4H), 4.18 (dd, J=16.0, 8.0 Hz, 1H), 3.94-4.05 (m, 2H), 3.55 (dd, J=9.5, 7.4 Hz, 1H), 3.37 (conformation 1) and 3.32 (conformation 2) (s, 3H), 3.33 (conformation 2) and 3.27 (conformation 1) (s, 3H), 3.19 (s, 3H), 1.76 (hexatet, J=6.9 Hz, 2H), 1.20-1.44 (m, 10H), 0.87 (t, J=6.9 Hz, 3H); $^{13}$C NMR (CDCl$_3$, 75 MHz) δ 191.07, 151.07, 150.99, 144.49, 144.46, 144.38, 136.06, 136.03, 135.96, 135.93, 135.87, 135.77, 135.35, 135.33, 135.22, 134.45, 134.42, 134.41, 128.93, 128.88, 128.85, 128.74, 128.65, 128.59, 128.57, 128.55, 128.50, 128.16, 128.05, 128.00, 127.92, 124.82, 124.80, 124.66, 121.84, 121.79, 111.86, 98.89, 97.74, 96.75, 77.71, 77.40, 77.36, 77.01, 75.75, 74.41, 70.82, 70.74, 70.03, 69.94, 69.84, 69.79, 69.77, 69.72, 69.57, 69.50, 69.27, 56.83, 55.99, 55.93, 55.90, 31.92, 29.41, 29.39, 29.34, 29.06, 25.94, 25.91, 22.75, 14.22; $^{31}$P NMR (CDCl$_3$, 162 MHz) δ conformation 1: −0.07 (2P), −6.05 (1P); conformation 2: −0.10 (2P), −625 (1P); ESI (Pos)-HRMS for [M+Na]$^+$ C$_{62}$H$_{77}$O$_{20}$P$_3$Na: calcd 1257.4119, found 1257.4169.

Compound 7

Aldehyde 6 (30 mg, 24 mol) in anhydrous THF (2.0 mL) was treated with NaBH$_4$ (5.0 mg, 0.132 mmol) at r.t. under argon for 4 h. The reaction mixture was concentrated and purified by column chromatography (hexane:acetone=2:1) to give the product 7 (28 mg, 95%) as colorless oil. $^1$H NMR (CDCl$_3$, 400 MHz) δ 7.25-7.38 (m, 26H), 6.95 (s, 1H), 6.83 (d, J=8.2 Hz, 1H), 5.23-5.27 (m, 2H), 4.85-5.17 (m, 9H), 4.58-4.76 (m, 6H), 4.50 (dd, J=6.9, 6.3 Hz, 1H), 4.08-4.44 (m, 5H), 3.81-3.98 (m, 2H), 3.50 (dd, J=11.3, 10.2 Hz, 1H), 3.36 (conformation 1) and 3.32 (conformation 2) (s, 3H), 3.33 (conformation 2) and 3.27 (conformation 1) (s, 3H), 3.19 (s, 3H), 1.76 (tt, J=7.4, 7.0 Hz, 2H), 1.20-1.44 (m, 10H), 0.87 (t, J=6.5 Hz, 3H); $^{13}$C NMR (CDCl$_3$, 100 MHz) δ 150.45, 150.40, 139.32, 139.27, 138.98, 138.91, 136.26, 136.16, 136.15, 136.07, 135.79, 135.71, 128.67, 128.60, 128.52, 128.44, 128.35, 128.20, 128.15, 128.04, 127.84, 121.75, 121.72, 121.47, 121.45, 118.97, 118.91, 112.46, 98.84, 97.72, 96.60, 96.36, 78.87, 77.36, 75.69, 75.60, 74.50, 74.41, 74.17, 70.42, 70.12, 69.86, 69.80, 69.70, 69.64, 69.60, 69.54, 69.35, 69.30, 69.09, 69.05, 65.10, 56.87, 56.85, 55.94, 55.88, 31.96, 29.49, 29.46, 29.38, 29.31, 26.04, 26.00, 22.78, 14.24; $^{31}$P NMR (CDCl$_3$, 162 MHz): δ conformation 1: 0.07 (2P), −5.34 (1P); conformation 2: 0.04 (2P), −5.44 (1P); ESI-HRMS for [M+Na]$^+$ C$_{62}$H$_{79}$O$_{20}$P$_3$Na: calcd 1259.4275, found 1259.4267. The $^{31}$P NMR signals of the two conformers collapsed when the temperature of measurement increased to 50° C.

Compound WH-15

A mixture of compound 7 (20 mg, 16 μmol), 4-Dimethylaminopyridine (DMAP) (12 mg, 100 μM) and N-(quinolin-6-yl)-1H-imidazole-1-carboxamide 8 (12 mg, 50 μmol) was stirred in anhydrous acetonitrile (3.0 mL) under argon at 60° C. The reaction was monitored by TLC (Hexane:acetone=1: 1) on silica gel. After 4 h, the reaction mixture was concentrated and subjected to a flash column purification (Hexane: acetone=1.5:1) to remove most of the starting material 6 and DMAP. The purified compound 9 was dried and re-dissolved in anhydrous CH$_2$Cl$_2$ (2.0 mL). Bromotrimethylsilane (2.0 mL) was then added at −10° C. under argon. The reaction mixture was slowly warmed to r.t. and stirred for another 2 h. The solvents and volatile compounds were removed by evaporation, and the residue was dried under vacuum for 1 h. Methanol (4.0 mL) was subsequently added and stirred at r.t. for 2 h. After removal of the solvent, the residue was dried under vacuum for 2 h. Then the crude product was re-dissolved in 30% MeOH and purified by HPLC on a Thermo Betasil C18 reverse Phase column (150×10 mm, 5 μm). The desired fractions were combined to give the product (5 mg, 36%) as white solid. The compound was treated with 1.0 M TEAB buffer to form the triethyl amine salt, which was stable at −20° C. for 2 months. $^1$H NMR (CD$_3$OD, 400 MHz) δ 8.6 (d, J=3.6 Hz, 1H), 8.16 (d, J=8.4 Hz, 1H), 8.06 (s, 1H), 7.84 (d, J=9.0 Hz, 1H), 7.66 (d, J=9.0 Hz, 1H), 7.48 (d, J=8.2 Hz, 1H), 7.39 (dd, J=8.4, 4.3 Hz, 1H), 6.96 (s, 1H), 6.84 (d, J=7.7

Hz, 1H), 5.06 (s, 2H), 4.30 (dd, J=17.9, 8.8 Hz, 1H), 4.22 (br. s, 1H), 4.07 (dd, J=7.7, 8.4 Hz, 1H), 3.85-3.96 (m, 4H), 3.51 (d, J=9.3 Hz, 1H), 1.71 (tt, J=7.8, 6.9 Hz, 2H), 1.30-1.41 (m, 2H), 1.10-1.30 (m, 8H), 0.77 (t, J=6.9 Hz, 3H); $^{13}$C NMR (CD$_3$OD, 126 MHz) δ 155.89, 151.52 (d, J=6.0 Hz), 149.63 (d, J=9.9 Hz), 145.55, 144.06 (d, J=6.0 Hz), 139.17, 137.86, 133.54, 130.70, 129.78, 124.59, 123.05, 122.42, 121.74, 115.46, 115.41, 115.29, 80.22, 78.36, 72.94 (d, J=9.9 Hz), 72.39, 70.57, 67.82, 60.28, 33.18, 30.70, 30.62, 30.53, 27.23, 23.87, 14.61; $^{31}$P NMR (CD$_3$OD, 162 MHz) δ 3.88 (1P), 3.11 (1P), −3.39 (1P); ESI (Pos)-HRMS for [M+H]$^+$ C$_{31}$H$_{44}$N$_2$O$_{18}$P$_3$: calcd 825.1799, found 825.1793.

Phospholipase A2 (PLA2) Assay

The reporter WH-15 (50 μM) was dissolved in the assay buffer (10 μL) that contains 150 mM of NaCl and 5 mM of CaCl$_2$ at 37° C. The assay was initiated by the addition of 2 μL of PLA2 (10 unit/mL, Sigma). The fluorescence was measured as described above. For the control reaction to demonstrate PLA2 is functional, dioleoylphosphatidylcholine (DOPC) was used instead of WH-15 under otherwise identical conditions. The enzymatic product lysophosphatidylcholine was detected by $^{31}$P-NMR and mass spectrometry (MS). The specific activity of PLA2 was measured as 5.9 nmol/min/unit.

Phospholipase D (PLD) Assay

The reporter WH-15 (50 μM) was dissolved in the assay buffer (10 μL) that contains 12.4 mM of Tris (pH 8.4), 3.1 mM of SDS, and 50 mM of CaCl$_2$. The assay was initiated by the addition of 2 μL of PLD (10 unit/mL, Sigma). The fluorescence was measured as described above. For the control reaction to demonstrate PLD is functional, DOPC was used instead of WH-15 under otherwise identical conditions. The enzymatic product dioleoylphosphatidic acid (DOPA) was detected by mass spectrometry (MS) and $^{31}$P-NMR. The specific activity of PLD was measured as 14.4 nmol/min/unit.

Assay with Mammalian PLC Isoforms

All fluorescence assays were performed in Perkin-Elmer 384-well plates, and the fluorescence was recorded on a Perkin-Elmer Wallac Envision 2103 Multilabel Reader with the excitation wavelength of 355 nm (ex filter 355 nm, 10 nm) and the emission wavelength of 535 nm (em filter 535 nm, 10 nm). To carry out the assay, the reporter WH-15 (44 μM, final concentration) was dissolved in the assay buffer (15 μL) that contains 133 μg/mL fatty-acid free BSA, 50 mM HEPES (pH 7.2), 70 mM KCl, 3 mM CaCl$_2$, 3 mM EGTA, and 2 mM DTT at 37° C. Assays were initiated upon addition of 20 ng of purified PLC protein, and data were recorded every 2 min. Experiments were repeated at least three times. The excitation and emission spectra were recorded on a QM-4 PTI Spectral Fluorometer. Equivalent amounts of purified PLCs (3 μg, inset) were verified by SDS-PAGE followed by staining with Coomassie Brilliant Blue.

Kinetic Studies of WH-15 and Endogenous PIP$_2$.

The reporter WH-15 was dried under a stream of argon and resuspended in 20 mM HEPES containing 0.5% cholate. This solution was diluted to obtain final assay conditions with 175, 117, 47, 35, 29, 23, 12, or 6 μM WH-15 in the assay buffer (10 mM HEPES, pH 7.4, 120 mM KCl, 10 mM NaCl, 2 mM EGTA, 5.8 mM MgSO$_4$, 0.5% cholate, 160 μg/μL fatty-acid-free BSA, and 100 μM free Ca$^{2+}$) in a final volume of 12 μL. The assays were started by the addition of 4 ng of purified full-length wild-type PLC-γ1. The reaction mixtures were then incubated at 30° C., and fluorescence was measured continuously as described above. For kinetic studies with the endogenous PIP2, a mixture of PtdIns-(4,5)P2 (300 μM, Avanti Polar Lipids) and ~10,000 cpm of [$^3$H]PtdIns-(4,5)P2 was dried under a stream of nitrogen and resuspended in 0.5% cholate. The resulting lipid stock was diluted to obtain final assay conditions with either 280, 160, 80, 24, or 8 μM PtdIns (4,5)P2 in the same buffer as described above in a final volume of 60 μL. Assays were initiated by the addition of 17 ng of purified full-length wild-type PLC-γ1. After incubation at 30° C. at time intervals between 0-8 min, reactions were stopped by the addition of 200 μL of 10% (v/v) trichloroacetic acid (TCA) and 100 μL of 10 mg/mL BSA to precipitate uncleaved lipids and protein. Centrifugation of the reaction mixture isolated soluble [$^3$H]Ins(1,4,5)P3, which was quantified using liquid scintillation counting.

Transfected Cell Lysate Assay.

Cell lysates were prepared from transiently transfected HEK-293T cells plated in 12-well dishes at a cell density of 65,000 cells/well in Dulbecco's Modified Eagles Medium (DMEM) supplemented with 10% fetal bovine serum (FBS), 10,000 units/mL penicillin, 10,000 units/mL streptomycin, and 25 units/mL amphotericin B. Following incubation for 24 h at 37° C. in an atmosphere of 95% air/5% CO$_2$, cells were transfected with 600 ng of the indicated DNA and 100 ng of empty vector, for a total of 700 ng of DNA per well. DNA was complexed with FuGENE 6 transfection reagent (Roche Applied Sciences) in a 4:1 ratio of FuGENE 6 reagent to DNA prior to transfection. Twenty-four hours post transfection, media were aspirated and replaced with serum-free DMEM for 12-16 h. Subsequently, cells were lysed in 200 μL of RIPA buffer (Sigma) as per manufacturer's protocol. Lysates were normalized for total protein concentration using a Bio-Rad Protein assay (Bio-Rad Dye Reagent) prior to use in the reporter assay. Reporter assays were initiated by the addition of 50 μL of normalized cell lysate to the mixture (final volume 120 μL) that contains 50 μM reporter WH-15, 83 μg/mL fatty-acid free BSA, 50 mM HEPES (pH 7.2), 70 mM KCl, 3 mM CaCl$_2$, 3 mM EGTA, and 2 mM DTT at 37° C. Data was collected every 3 min using a Wallac Victor$^2$ 1420 Multilabel Counter (model 1420-011, Perkin-Elmer Life Sciences) with an excitation wavelength of 340 nm and an emission wavelength of 535 nm. Western blotting was performed on normalized cell lysates to confirm the expression of PLC-β2, -β1, and -γ1 using monoclonal antibodies (Santa Cruz).

REFERENCES

1. Harden, T. K.; Sondek, J. *Annu. Rev. Pharmacol. Toxicol* 2006, 46, 355-79.
2. Rhee, S. G. *Annu. Rev. Biochem.* 2001, 70, 281-312.
3. Lemmon, M. A., *Nat. Rev. Mol. Cell Biol.* 2008, 9, 99-111.
4. Selected references: a) Kassis, J. et al. *Clin. Cancer Res.* 1999, 5, 2251-60. b) Cocco, L.; Manzoli, L.; Palka, G.; Martelli, A. M. *Adv. Enzyme Regul.* 2005, 45, 126-35. c) Shepard, C. R.; Kassis, J.; Whaley, D. L.; Kim, H. G.; Wells, A. *Oncogene* 2007, 26, 3020-6. d) Shimohama, S. et al. *Ann. N.Y. Acad. Sci.* 1993, 695, 46-9. e) Matsushima, H.; Shimohama, S.; Fujimoto, S.; Takenawa, T.; Kimura, J. *Alzheimer Dis. Assoc. Disord.* 1995, 9, 213-7. f) Shi, T. J. et al. *Proc. Nat.l Acad. Sci. U.S.A.* 2008, 105, 20004-8.
5. Wilsher, N. E. et al. *Drug. Metab. Dispos.* 2007, 35, 1017-22.
6. a) Zaikova, T. O. et al. *Bioconjug. Chem.* 2001, 12, 307-13. b) Birrell, G. B. et al. *Biophys. J.* 2003, 84, 3264-75. c) Rukavishnikov, A. V. et al. *Bioorg. Med. Chem. Lett.* 1999, 9, 1133-1136. d) Hendrickson, E. K.; Johnson, J. L.; Hendrickson, H. S. *Bioorg. Med. Chem. Lett.* 1991, 1, 619-623.
7. a) Lee, M. R.; Baek, K. H.; Jin, H. J.; Jung, Y. G.; Shin, I. *Angew. Chem. Int. Ed. Engl.* 2004, 43, 1675-8. b) Pez, D. et al. *Bioorg. Med. Chem.* 2003, 11, 4693-711
8. Kubiak, R. J.; Bruzik, K. S. *J. Org. Chem.* 2003, 68, 960-8.

9. Ellis, M. V. et al. *J. Biol. Chem,* 1998, 273, 11650-9.
10. Hicks, S. N. et al. *Mol. Cell* 2008, 31, 383-94, Example 2

Figure 8:
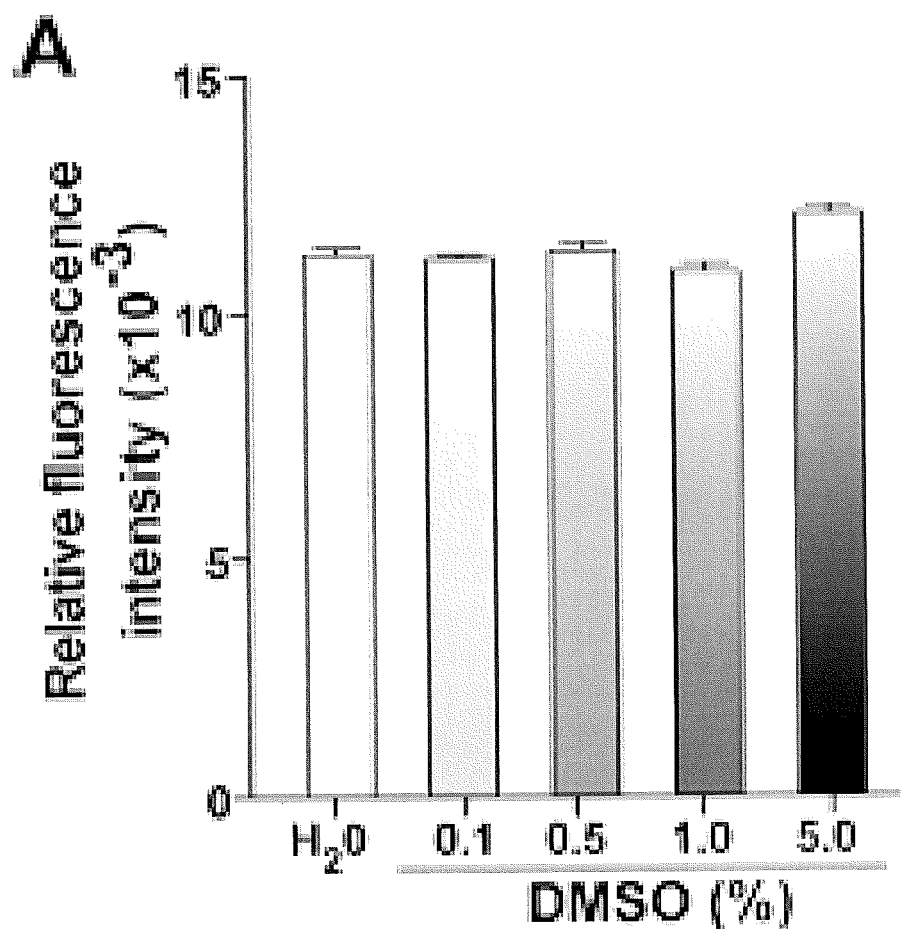
FIG. 8. (A) WH-15 (50 μM) was incubated with 100 ng of purified PLC-δ1 in the presence of the indicated concentrations of DMSO at 32° C. for 30 min. (B) WH-15 (50 μM) hydrolysis was measured after incubation with the indicated proteins. (C) The Z'-factor was calculated using ten parallel experiments in which WH-15 (50 μM) was incubated with 100 ng of PLC-δ1 or PLC-δ1 (E341A) at 32° C. for 30 min In all cases, fluorescence was recorded using 355/535 nm filters and normalized to initial fluorescence.
Figure 8:
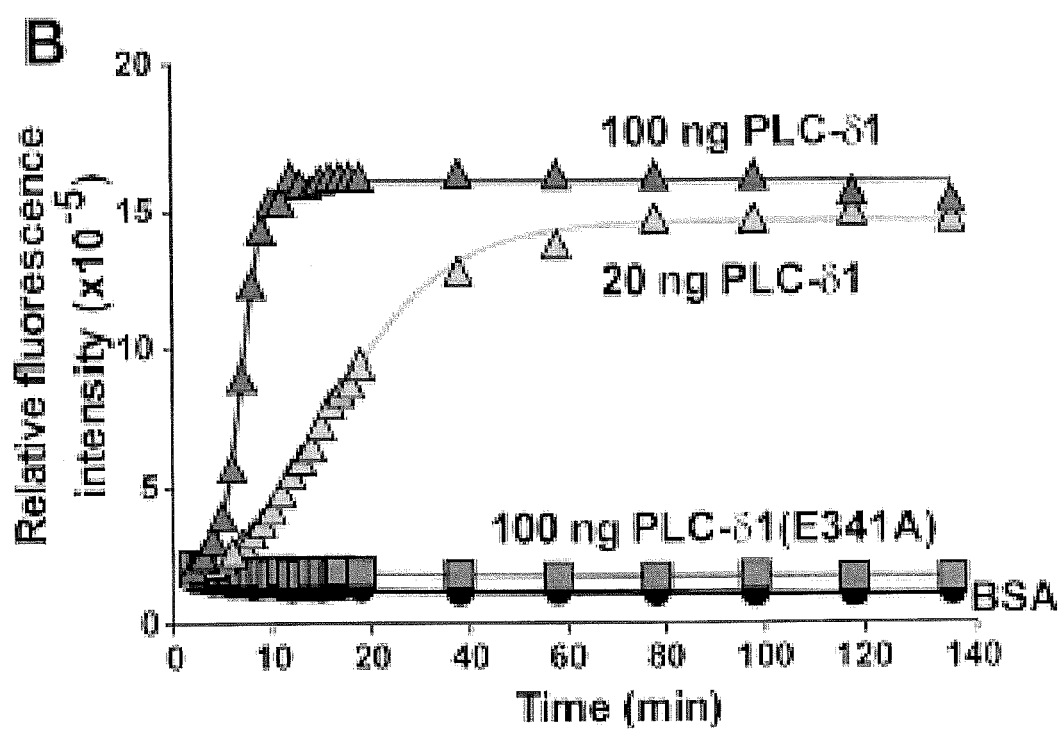
Figure 8:
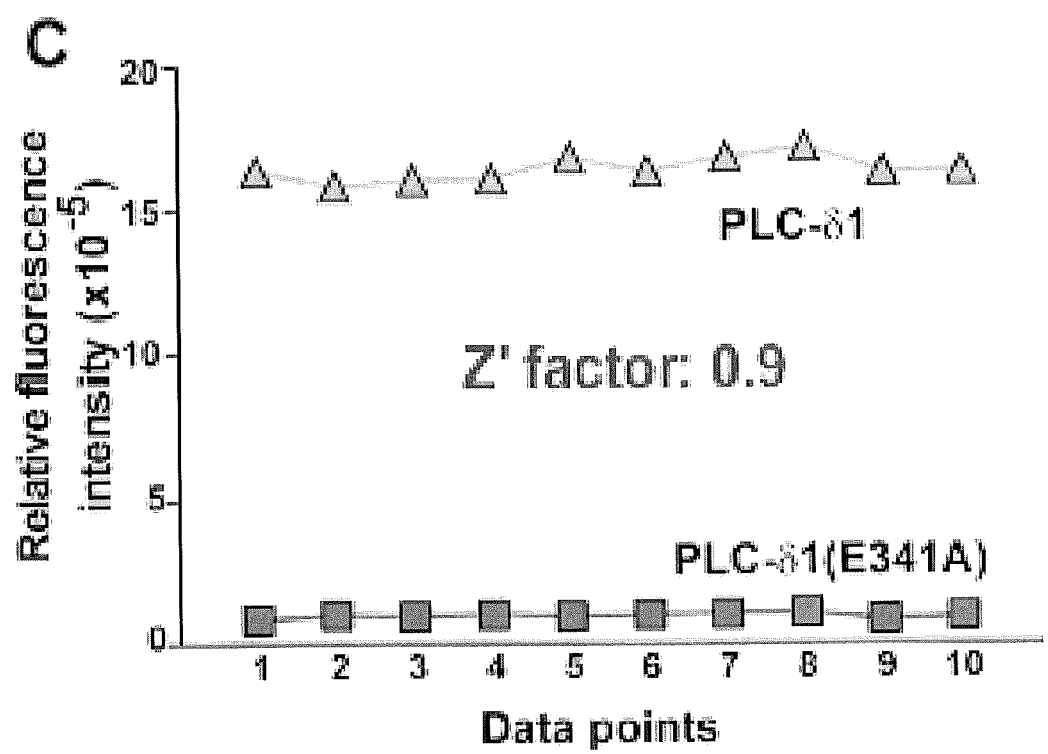

An assessment was made on whether WH-15 and PLC-δ1 could be used to implement a prototype assay suitable of configuration for high-throughput screens using 96-well microtiter plates (FIG. 8). The results demonstrated that the capacity of PLC-δ1 to hydrolyze WH-15 was unaffected by up to 5% DMSO, and typically much less DMSO is used to solubilize libraries of small molecules (FIG. 8A). Furthermore, the hydrolysis of 50 µM WH-15 by as little as 20 ng of wild-type PLC-δ1 is sufficient to generate an approximately 15-fold increase in fluorescence over the course of one hour (FIG. 8B). In contrast, in the absence of PLC-δ1 or in the presence of a catalytically inactive form (E341A), no increase in fluorescence occurred over the same time. Indeed, WH-15 is stable for up to 24 hrs at room temperature over a pH range of 7-10 as judged by thin layer chromatography (TLC) analysis. Finally, differences in fluorescence upon the incubation of WH-15 with either wild-type or catalytically inactive PLC-δ1 in multiple wells of a 96-well microtiter plate were used to calculate an initial Z'-factor of 0.9 indicating that this format should be highly reproducible for high-throughput screening (FIG. 8C).

Similar amounts of PLC-δ1, -β2, and -γ1 would be expected to be required for screening since the three isozymes hydrolyzed WH-15 with similar rates (FIG. 1B).

The experiments described above indicate that the hydrolysis of WH-15 by PLC-δ1 can be measured reproducibly in a microtiter-based format. Parameters that can be optimized to produce a high throughput screen include: i) order of reagent addition, ii) concentrations of WH-15 and PLC-δ1, iii) reaction time, and iv) potential stop conditions. The final assay entailed the incubation of 4 ng of PLC-δ1 (4 µl) with 10 µM WH-15 (2 µl of a 50 µM stock) in a final volume of 10 µl for 60 minutes at room temperature prior to terminating phospholipase activity with a final concentration of 60 mM EGTA (5 µl), which chelates $Ca^{2+}$ and abrogates catalysis. The fluorescence values ($\lambda_{em}/\lambda_{ex}$=355/535 nm with 10 nm bandwidth) for these conditions were measured in two 384-well plates for three consecutive days. Identical conditions with 4 ng of BSA in place of PLC-δ1 were measured in parallel. From these two sets of conditions, the average Z factor from all plates was 0.75. For these conditions it was calculated that the rate of hydrolysis of WH-15 is linear with less than 30% of total WH-15 consumed as judged by the fluorescence intensity of the reaction mixture compared to those of pure 6-aminoquinoline at various concentrations.

Figure 9:
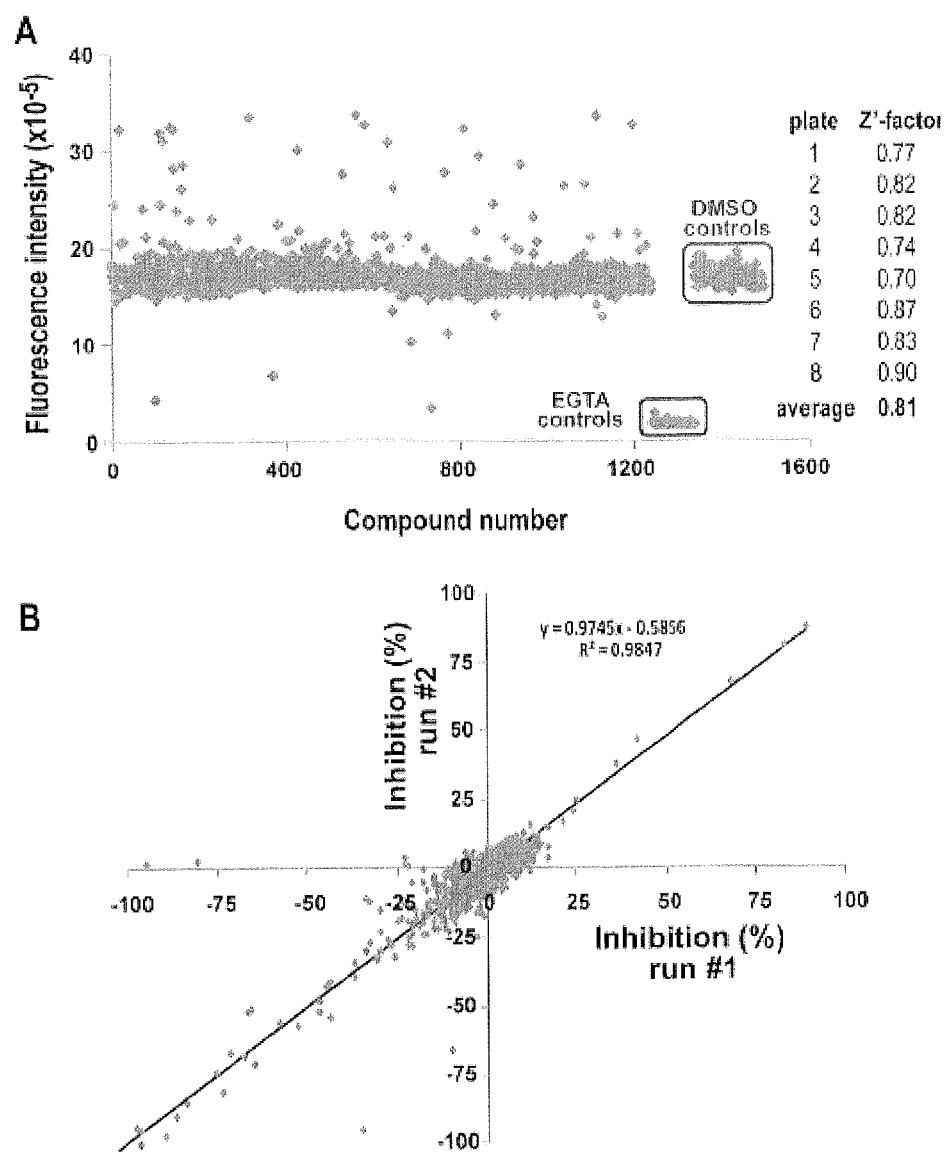
FIG. 9. (A) Scatter plot of fluorescence changes after incubation of PLC-δ1 and WH-15 with individual compounds of the LOPAC1280 collection. The Z'-factor for the screen is 0.81 with a hit rate of 0.23% for greater than 50% inhibition relative to DMSO. (B) Screen reproducibility. The correlation coefficient for two parallel screens of the LOPAC1280 library was 0.98.

Using essentially the conditions described above, the 1280 compounds comprising the Library Of Pharmacologically Active Compounds 1280 (LOPAC1280; Sigma-Aldrich) were screened in duplicate (FIG. 9). Two µl of a 50 µM stock of each compound was incubated with 4 ng of PLC (4 µl) for 10 min prior to incubation with 10 µM WH-15 in a final volume of 10 µl. The correlation coefficient for the parallel runs was 0.98 with an average Z'-factor of 0.81 for all plates (DMSO versus EGTA). The hit rate was 0.23% for compounds (10 µM) exhibiting greater than 50% inhibition relative to identical reactions containing DMSO alone. While this format exhibits excellent characteristics for a high-throughput screen, it is noted that identification of a disproportionate number of putative activators relative to inhibitors of PLC-δ1. The majority of these putative activators most likely represent false hits due to high intrinsic fluorescence. This will be confirmed by incorporating a secondary counter-screen using catalytically-inactive PLC-δ1. Overall, the high signal-to-noise ratio and reproducibility should ensure the successful identification of both activators and inhibitors of PLCs.

Current protocols for the synthesis of WH-15 are adequate to carry out screening studies. For example, the current scheme for the synthesis of WH-15 (Scheme 3) typically yields approximately 3 mg of this reporter with greater than 95% purity per small-scale synthesis that starts with 50 mg of compound 5. Approximately 1 mg of WH-15 was consumed in the screening of the LOPAC1280 library with PLC-δ1: (0.3 µg WH-15 per well×384 wells per plate×4 plates per run×2 runs). Similarly, it is estimated that approximately 4 mg of WH-15 will be required to screen a 5000 compound library with PLC-δ1. Therefore, multiple small scale syntheses of WH-15 will provide sufficient WH-15 to screen PLC-δ1. Similar logic essentially guarantees capacity to produce sufficient WH-15 to screen PLC-β2 and -γ1, especially since all isozymes hydrolyze WH-15 with similar rates (FIG. 1B). WH-15 has been produced several times as described with similar yield and high purity as measured by LC-MS, $^1$H-NMR, and $^{31}$P-NMR. These batches were stable for longer than 6 months at −80° C. as verified using similar techniques.

Figure 10:
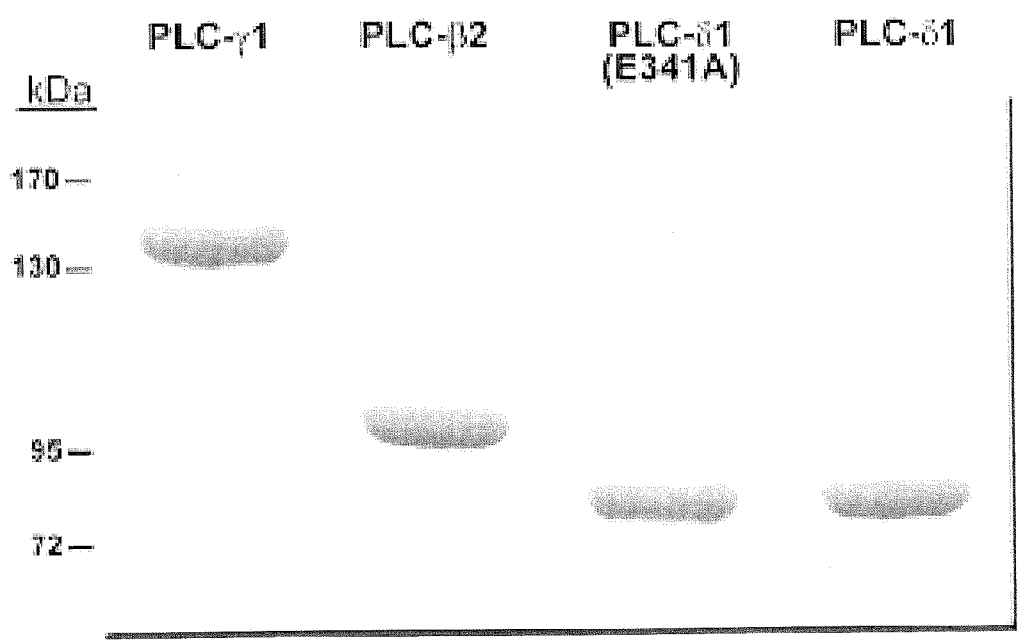
FIG. 10. Coomassie stained gel of 2 μg of the indicated PLC isozymes. All isozymes are produced in multi-milligram yields.

Based on the preliminary screens of PLC-δ1, sufficient amounts of purified PLCs can be produced for screening studies, including high-throughput screens. For example, screening the LOPAC1280 library consumed approximately 12 µg of purified PLC-δ1: (4 ng protein per well×384 wells per plate×4 plates per run×2 runs). Similarly, it should take approximately 50 µg of PLC-δ1 to screen a library of 5000 compounds (16 plates). Therefore, the screening studies should consume far less than 1 mg of purified PLC-δ1; over 10 mg of wild-type or catalytically-inactive PLC-δ1 per liter of bacteria over-expressing recombinant PLC-δ1 is routinely produced. Similarly, approximately 5 mg of highly active PLC-β2 or -γ1 per liter of insect cells were purified (FIG. 10). Since all three isozymes hydrolyze WH-15 with similar kinetics (FIG. 1B), it is anticipated that less than 1 mg of purified PLC-β2 or -γ1 will be sufficient to screen these isozymes. Moreover, the amounts of PLCs that can be purified essentially guarantee the ability to produce these enzymes in sufficient quantities of each isozyme to screen very large compound libraries, e.g., >100K.

The foregoing is illustrative of the present invention, and is not to be construed as limiting thereof. The invention is defined by the following claims, with equivalents of the claims to be included therein. All publications, patent applications, patents, patent publications, sequences identified by GenBank and/or SNP accession numbers, and other references cited herein are incorporated by reference in their entireties for the teachings relevant to the sentence and/or paragraph in which the reference is presented.

That which is claimed is:

1. A compound of Formula I:

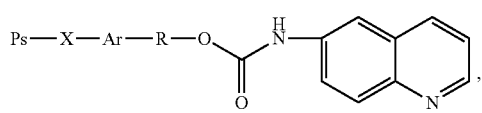

(I)

wherein:
Ps is a substrate for phospholipase C isozymes;
X is O or S;
Ar is an aromatic group which may be substituted with one or more functional groups selected from the group consisting of alkyl, alkenyl, alkynyl, hydroxy, hydroxyalkyl, alkoxy, aryloxy, alkylthio, amino, aminoalkyl, alkylamino, cycloalkyl, heteroaryl, heteroalkyl, aryl, arylalkyl, aliphatic oxide, $OC(=O)R_{10}$, $OC(=O)OR_{10}$, $OC(=O)N(R_{10})_2$, $O(CH_2)_mN(R_{10})_2$, $C(=O)N(R_{10})_2$, and $O(CH_2)_mCOOR_{10}$, where m is 1-20 and $R_{10}$ is H, alkyl, alkenyl, or alkynyl; and
R is alkyl, alkenyl, alkynyl, aryl, or arylalkyl.

2. The compound of claim 1, wherein Ps is an inositol phosphate, phosphatidylinositol, glycosylphosphatidylinositol, or an analog thereof.

3. The compound of claim 2, wherein Ps is selected from the group consisting of inositol phosphate analogues and glycosylphosphatidylinositol analogues.

4. The compound of claim 3, wherein Ps is an inositol 1,4,5-triphosphate analog.

5. The compound of claim 1, wherein X is O.

6. The compound of claim 1, wherein X is S.

7. The compound of claim 1, wherein Ar is phenyl.

8. The compound of claim 7, wherein the phenyl group is substituted in the ortho position.

9. The compound of claim 8, wherein the phenyl group is substituted in the ortho position with a functional group selected from the group consisting of alkyl, alkenyl, alkynyl, and alkoxy.

10. The compound of claim 1, wherein R is alkyl.

11. The compound of claim 1, wherein R is —$CH_2$—.

12. The compound of claim 1, wherein Ps is an inositol triphosphate analog, X is O, Ar is phenyl, and R is alkyl.

13. The compound of claim 12, wherein the phenyl group is substituted in the ortho position with a functional group selected from the group consisting of alkyl, alkenyl, alkynyl, and alkoxy, and R is —$CH_2$—.

14. The compound of claim 1, wherein the compound comprises a localization signal.

15. The compound of claim 1, wherein the compound comprises a photocage group.

16. A compound of Formula II:

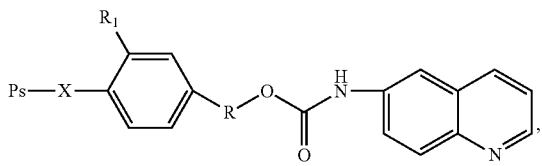

(II)

wherein:

Ps is a substrate for phospholipase C isozymes;

X is O or S;

R is alkyl, alkenyl, alkynyl, aryl, or arylalkyl; and $R_1$ is selected from the group consisting of H, alkyl, alkenyl, alkynyl, hydroxy, hydroxyalkyl, alkoxy, aryloxy, alkylthio, amino, aminoalkyl, alkylamino, cycloalkyl, heteroaryl, heteroalkyl, aryl, arylalkyl, aliphatic oxide, OC(=O)$R_{10}$, OC(=O)O$R_{10}$, OC(=O)N($R_{10}$)$_2$, O(CH$_2$)$_m$N($R_{10}$)$_2$, C(=O)N($R_{10}$)$_2$, and O(CH$_2$)$_m$COO$R_{10}$, where m is 1-20 and $R_{10}$ is H, alkyl, alkenyl, or alkynyl.

17. The compound of claim 16, wherein Ps is an inositol phosphate, phosphatidylinositol, glycosylphosphatidylinositol, or an analog thereof.

18. The compound of claim 17, wherein Ps is selected from the group consisting of inositol phosphate analogues and glycosylphosphatidylinositol analogues.

19. The compound of claim 18, wherein Ps is an inositol 1,4,5-triphosphate analog.

20. The compound of claim 16, wherein X is O.

21. The compound of claim 16, wherein X is S.

22. The compound of claim 16, wherein is $R_1$ is selected from the group consisting of alkyl, alkenyl, alkynyl, and alkoxy.

23. The compound of claim 16, wherein Ps is an inositol 1,4,5-triphosphate analog, X is O, and $R_1$ is selected from the group consisting of alkyl, alkenyl, alkynyl, and alkoxy.

24. The compound of claim 16, wherein the compound comprises a localization signal.

25. The compound of claim 16, wherein the compound comprises a photocage group.

26. A compound of Formula III:

27. The compound of claim 26, wherein the compound comprises a photocage group.

28. The compound of claim 26, wherein the compound comprises a localization signal.

29. The compound of claim 26, wherein the compound has the following structure:

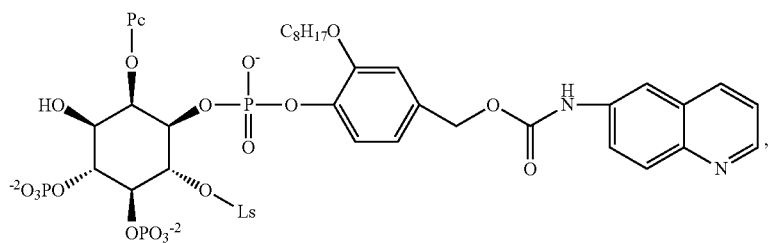

wherein:
Pc is a photocage group; and
Ls is a localization signal.

30. A compound of Formula IV:

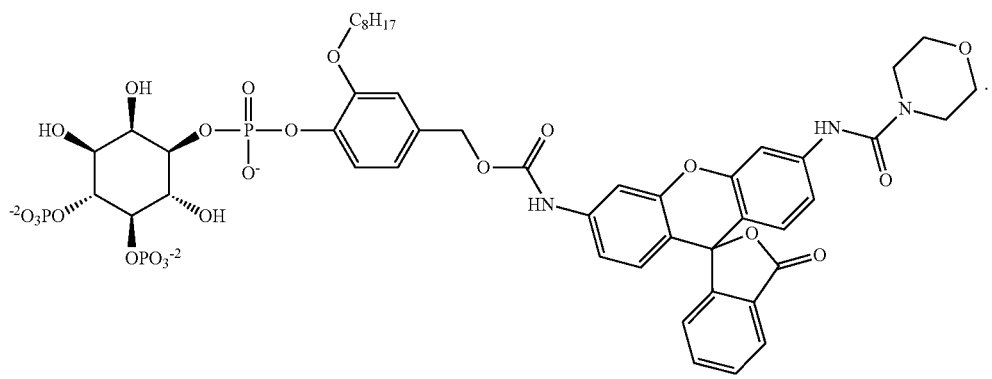

31. A method of identifying a test substance that inhibits phospholipase C activity, comprising:
   a) contacting the compound of claim 1 with phospholipase C in the presence of the test substance, under conditions whereby fluorescence resulting from reaction of the compound and phospholipase C can be detected, and detecting the amount of fluorescence;
   b) contacting the compound of (a) above with the phospholipase C of (a) above in the absence of the test substance, under conditions whereby fluorescence resulting from reaction of the compound and phospholipase C can be detected, and detecting the amount of fluorescence;
   c) comparing the amount of fluorescence detected in step (a) with the amount of fluorescence detected in step (b), whereby a decrease in the amount of fluorescence detected in step (a) identifies that the test substance inhibits phospholipase C activity.

32. The method of claim 31, wherein the test substance is a small molecule.

33. The method of claim 31, further comprising activating phospholipase C with a phospholipase C activator.

34. A method of detecting phospholipase C activity in a cell, comprising:
   a) contacting the compound of claim 1 with a cell under conditions whereby fluorescence resulting from reaction of the compound and phospholipase C can be detected; and
   b) detecting fluorescence in the cell, thereby detecting phospholipase C activity in the cell.

35. The method of claim 34, further comprising activating phospholipase C with a phospholipase C activator.

36. A method of detecting aberrant phospholipase C activity in a cell, comprising:
   a) contacting the compound of claim 1 with a cell under conditions whereby fluorescence resulting from reaction of the compound and phospholipase C can be detected;
   b) detecting an amount or pattern of fluorescence in the cell; and
   c) comparing the amount or pattern of fluorescence detected in step (b) with the amount or pattern of fluorescence in a control cell that has been contacted with the compound of step (a), whereby an alteration in the amount or pattern of fluorescence in the cell as compared with the control cell detects aberrant phospholipase C activity in the cell.

37. The method of claim 36, wherein the cell is a diseased cell.

38. The method of claim 36, wherein the alteration is an increase in the amount of fluorescence in the cell as compared with the control cell.

39. The method of claim 36, wherein the alteration is a decrease in the amount of fluorescence in the cell as compared to the control cell.

40. The method of claim 36, further comprising activating phospholipase C with a phospholipase C activator.

41. The method of claim 36, wherein the cell is from a subject at risk of having a disease.

42. The method of any of claim 36, wherein the cell is from a subject suspected of having a disease.

* * * * *

UNITED STATES PATENT AND TRADEMARK OFFICE
CERTIFICATE OF CORRECTION

PATENT NO. : 8,703,437 B2
APPLICATION NO. : 13/703274
DATED : April 22, 2014
INVENTOR(S) : Zhang et al.

It is certified that error appears in the above-identified patent and that said Letters Patent is hereby corrected as shown below:

In the Specification
Column 1, Line 24, STATEMENT REGARDING ELECTRONIC FILING OF A SEQUENCE LISTING:
   Please correct "5470-55_ST25.txt," to read -- 5470-555_ST25.txt, --

Column 5, Line 15: Please correct "PLC-M (A)" to read -- PLC-δ1 (A) --

Signed and Sealed this
Ninth Day of December, 2014

Michelle K. Lee
*Deputy Director of the United States Patent and Trademark Office*

SEQUENCE LISTING

<160> NUMBER OF SEQ ID NOS: 3

<210> SEQ ID NO 1
<211> LENGTH: 11
<212> TYPE: PRT
<213> ORGANISM: Artificial
<220> FEATURE:
<223> OTHER INFORMATION: LAMP-1 lysosomal localization signal sequence

<400> SEQUENCE: 1

Arg Lys Arg Ser His Ala Gly Tyr Gln Thr Ile
1               5                   10

<210> SEQ ID NO 2
<211> LENGTH: 23
<212> TYPE: PRT
<213> ORGANISM: Artificial
<220> FEATURE:
<223> OTHER INFORMATION: LAP lysosomal localization signal

<400> SEQUENCE: 2

Arg Leu Lys Arg Met Gln Ala Gln Pro Pro Gly Tyr Arg His Val Ala
1               5                   10                  15

Asp Gly Glu Asp His Ala Val
            20

<210> SEQ ID NO 3
<211> LENGTH: 20
<212> TYPE: PRT
<213> ORGANISM: Artificial
<220> FEATURE:
<223> OTHER INFORMATION: LIMP-2 lysosomal localization signal

<400> SEQUENCE: 3

Arg Gly Gln Gly Ser Thr Asp Glu Gly Thr Ala Asp Glu Arg Ala Pro
1               5                   10                  15

Leu Ile Arg Thr
            20